(12) United States Patent
Zvezdin et al.

(10) Patent No.: US 11,844,920 B2
(45) Date of Patent: Dec. 19, 2023

(54) MICRONEEDLE IMMUNOTHERAPEUTIC MULTI-COMPONENT SYSTEM AND A METHOD FOR VACCINATION

(71) Applicant: Microneedles Inc, Wilmington, DE (US)

(72) Inventors: Vasilii Nikolaevich Zvezdin, Perm (RU); Andrei Jurievich Pavlov, Naantali (FI)

(73) Assignee: Microneedles Inc, Wilmington, DE (US)

(\*) Notice: Subject to any disclaimer, the term of this patent is extended or adjusted under 35 U.S.C. 154(b) by 202 days.

(21) Appl. No.: 17/381,691

(22) Filed: Jul. 21, 2021

(65) Prior Publication Data

US 2022/0023605 A1 Jan. 27, 2022

Related U.S. Application Data

(60) Provisional application No. 63/055,363, filed on Jul. 23, 2020.

(51) Int. Cl.
*A61M 3/00* (2006.01)
*A61M 37/00* (2006.01)
*A61K 9/00* (2006.01)

(52) U.S. Cl.
CPC ........ *A61M 37/0015* (2013.01); *A61K 9/0021* (2013.01); *A61M 2037/0023* (2013.01);
(Continued)

(58) Field of Classification Search
CPC ...... A61M 37/0015; A61M 2037/0023; A61M 2037/0046; A61M 2037/0053;
(Continued)

(56) References Cited

U.S. PATENT DOCUMENTS

| 10,828,478 B2 | 11/2020 | McAllister et al. |
| 2015/0112250 A1* | 4/2015 | Kwon ............... A61K 39/00 604/46 |
| 2016/0136407 A1 | 5/2016 | Falo, Jr. et al. |

FOREIGN PATENT DOCUMENTS

| WO | 2006101459 A1 | 9/2006 |
| WO | 2020232394 A1 | 11/2020 |

OTHER PUBLICATIONS

International Search Report and Written Opinon of PCT/US2021/042503, dated Nov. 5, 2021; 7p.

\* cited by examiner

*Primary Examiner* — Amber R Stiles
(74) *Attorney, Agent, or Firm* — Meunier Carlin & Curfman LLC

(57) ABSTRACT

A dissoluble microneedle drug delivery system includes a fixation component having an opening window area, and at least two replaceable and/or dissoluble inner matrices fitting into the window area one after another. The fixation component comprises an array of microneedles attached on its base, at least part of the microneedles being configured to fix the delivery system onto skin. The first inner matrix comprises a multitude of microneedles attached on its base, at least part of the microneedles configured to prepare the skin to vaccination by the subsequent second inner matrix. The second inner matrix is a vaccine/immunization matrix configured to replace the first inner matrix and comprising an array of microneedles attached on its base, at least part of the microneedles configured to deliver a vaccination. The system may include a microchannel network within at least one inner matrices for delivery of components regulating dissolution of the microneedles.

24 Claims, 23 Drawing Sheets

(52) U.S. Cl.
CPC ............... *A61M 2037/0046* (2013.01); *A61M 2037/0053* (2013.01); *A61M 2037/0061* (2013.01); *A61M 2202/30* (2013.01); *A61M 2205/0238* (2013.01); *A61M 2209/088* (2013.01)

(58) Field of Classification Search
CPC ...... A61M 2037/0061; A61M 2202/30; A61M 2205/0238; A61M 2209/088; A61K 9/0021; A61K 31/00; A61K 47/26; A61K 38/00
See application file for complete search history.

FIG. 13A-B a)
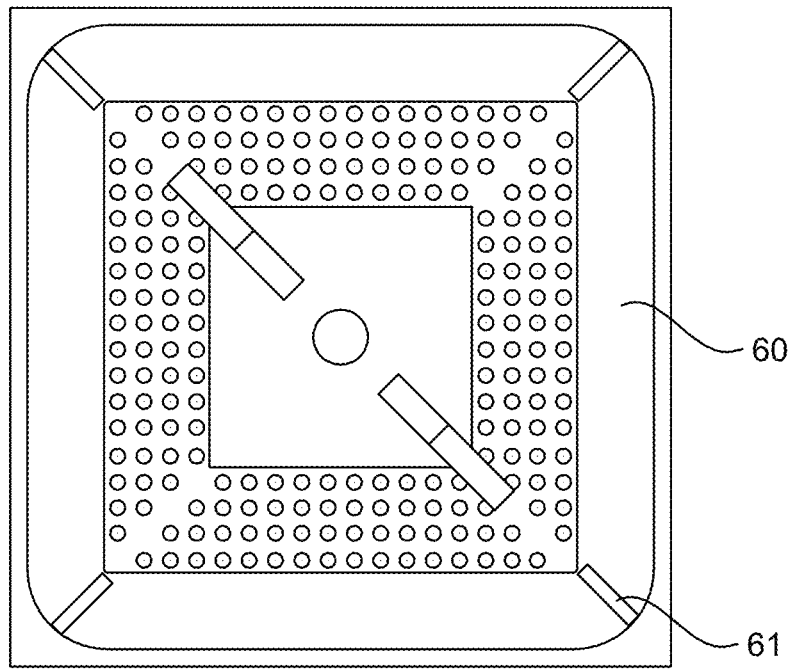
b)
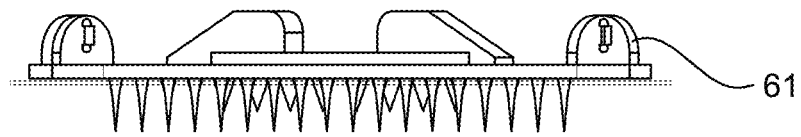
FIG. 17A-B a)　　　　　　　　　b)

FIG. 20A-B

MICRONEEDLE IMMUNOTHERAPEUTIC MULTI-COMPONENT SYSTEM AND A METHOD FOR VACCINATION

PRIORITY

This application claims priority of U.S. provisional application No. 63/055,363 filed on Jul. 23, 2020 the content of which is incorporated herein by reference.

FIELD OF THE INVENTION

The present invention generally relates to a medical transdermal drug delivery system (an integrated microneedle vaccination matrix) and medical vaccination methods, and particularly, to use of the medical drug delivery system for transdermal vaccination using dissoluble microneedle matrices. The system is particularly useful for vaccination of adult humans.

BACKGROUND OF THE INVENTION

Traditionally vaccines are administered as intramuscular or subcutaneous injections. These delivery methods are generally associated with pain, needle stick injuries and needle-phobia. Moreover, administration of vaccines by injections requires trained personnel.

In alternative that is gaining increasing interest is transdermal vaccine administration. The afferent immune link in the skin is represented by two variants of dendritic cells i.e., ordinary myeloid dendritic cells and Langerhans cells. Both of the dendritic cell types absorb foreign material, process it, migrate to regional lymph nodes and present the antigen to the T-lymphocytes.

Activation of Langerhans cells, cross-representing dendritic cells, has been established as an element of development of the immune response during transdermal administration of antigen (Chiu et. al. 2007; Pediatrics No. 119; p. 1076-1982). Improving administration of immunostimulants and vaccines is a vital field of scientific research and medical treatments today. Development of microneedle applicators capable of penetrating through the stratum corneum of the skin and dissolving in the epidermis and dermis, releasing antigens of various structures and molecular weights (proteins, polysaccharides, capsids, whole cells, DNA/mRNA vaccines), has become widespread. These systems allow administration of vaccines targeted to immunocompetent cells localized in the epidermis and dermis (Langerhans cells) painlessly and non-traumatically and to ensure the formation of an immune response to the introduced antigens (US20130110078A1; U.S. Pat. No. 8,911,749B2).

There are two approaches in the development of this technology. One approach, for example WO2019231360, is aimed at optimizing the introduction of microneedles into the hyper-elastic structure of the skin and reducing application time by rapidly dissolving microneedles or their individual layers. Another approach disclosed e.g., US20130110078A1, is aimed at increasing the efficiency of immunization during vaccination. This includes prime-boost vaccination, where the initial vaccine is injected into the skin using microneedles with a small total volume (microneedle volume is between 0.0005 and 0.014 mm$^3$) for initial immunization, and after some while microneedles with a large volume (large total microneedle volume is at least 0.05 mm$^3$) carry out a booster injection to further increase the immune response to protective levels (usually after the immune memory against this antigen decreases over time).

Delivery of pharmaceutical preparations based on DNA/mRNA is described, for example in US20050080028A1. The described microneedle devices are aimed at increasing the efficiency of DNA/mRNA introduction and transfection and include agents that increase transfection and inhibitors of nucleases (enzymes that destroy DNA and RNA molecules) and/or are equipped with additional electrodes for electroporation/sonoporation, etc.

It is, however, also known that when an array of microneedles is introduced into an elastic material, the mechanical stress on microneedles is distributed unevenly. Eriketi et al. (Eur. J. Pharm. Biopharm 2016, 107: 1-6) reported that the stress is higher on the microneedles located closer to the center of the array. With decrease of skin elasticity due to age-related changes, a significant increase of stress on individual groups of microneedles can occur. Moreover, the epidermal dehydration may slow down the dissolution of polymer microneedles, including fast-dissolving microneedles such as described in WO2019231360.

Furthermore, taking into account the decrease in the number of immunocompetent cells in the epidermis of the aged skin, the introduction of vaccines and further maintenance of the immune response by booster injections may not be sufficient and additional involvement of Langerhans cells to the vaccination site before the introduction of the vaccine itself would be necessary.

Thus, as it stands now, there is an acute and an unmet need of novel and efficient systems for delivering transdermal vaccination. Especially systems taking into account features such as age-related changes and dehydration of the epidermis, decrease of elasticity of the skin, and number of Langerhans cells.

Furthermore, there is a need for a vaccination system that can address the increased need for vaccination during emergency situations, such as pandemics, when vaccination may need to be administered by untrained persons or may need to be administered by the person him/herself.

With the above in mind, this disclosure now provides surprising and novel solutions over the prior art and the previously mentioned limitations. This, in turn, holds great promise and provides improved transdermal vaccination of the skin, subject to age-related changes and characterized by dehydration of the epidermis.

SUMMARY OF THE INVENTION

An object of the present invention is to improve transdermal vaccination of the skin, subject to age-related changes and characterized by dehydration of the epidermis, a decrease in the number of Langerhans cells and loss of elasticity.

An object of the present invention is to decrease mechanical resistance of the skin for overcoming spring resistance of the skin for vertical penetration.

An object of the present invention is to reduce application (vaccination) time. The longer the procedure, the stronger is the spring resistance of the skin on the dissoluble microneedles as the structure of the microneedles changes during dissolution and they are pushed out. The accuracy of the injection decreases with time, and the deviation cannot be compensated by pressing force as was though before.

An object of the present invention is to decrease immune response by increasing concentration of the target cells in the injection region. The more cells in the application (vaccination) region, the higher efficiency of the response. Furthermore, the penetration depth is not a (dominated) correlation factor. More important factors are the injected skin surface area and density of cells.

In order to solve the problems of prior art, this disclosure provides vaccination process that includes at least two steps and a system suitable for the two-step process. The first stage is preparation of the skin to the vaccination. The second step is the vaccination/immunization. The preparation and vaccination steps according to the invention use different matrices (also called patches) of dissoluble microneedles. In order to apply multiple matrices one after another, the system according to this disclosure may include a fixation frame attached to the skin for the time of the two-step vaccination process and to adapt the different matrices.

It is an object of this invention to provide a dissoluble microneedle drug delivery system, comprising: an outer micro-needle matrix, and at least a first and a second inner microneedle matrices. The outer microneedle matrix may optionally be mounted on a fixation frame. The outer microneedle matrix has an opening window in its center and a microneedle array affixed on its base. The microneedle array comprises microneedles of different lengths such that the longest microneedles are located close to the outer edges of the outer matrix and the shorter microneedles are located around the opening window area. The longest microneedles of the outer matrix are used for fixation of the matrix onto the skin and additionally may be used to delivery of an adjuvant. The shorter microneedles are mainly used for adjuvant preparation of the skin. The first inner matrix fits into the opening window area of the outer matrix and has a microneedle array affixed on its base. The microneedle array of the first inner matrix comprises dissoluble microneedles containing skin preparation components configured to prepare skin underneath the matrix for vaccination/immunization. The first inner matrix is also called skin preparation component. The second inner matrix, also called as vaccination/immunization component, is configured to fit into the opening window after the first matrix has been removed or it is dissolved. The second inner matrix has a microneedle array affixed on its base. The microneedle array comprises dissoluble microneedles containing vaccination/immunization components. The first inner matrix is dissoluble and/or removable and the second inner matrix is configured to replace the first inner matrix when the first inner matrix is dissolved or removed.

In certain embodiments the outer matrix and the first inner matrix are provided as one element and the first inner matrix is configured to completely dissolve while attached onto the skin and thus leave an opening window for the second inner matrix to be inserted into. In certain embodiments the base of the first inner matrix is not soluble and it is to be removed from the skin once the microneedles of the first inner matrix are dissolved.

It is still another object to provide the dissoluble microneedle drug delivery system, wherein the basic component of the microneedles is a soluble bio-polymer that dissolves in the skin due to fermentation.

It is still another object to provide the dissoluble microneedle drug delivery system, wherein at least part of the microneedles of the outer matrix include an adjuvant component selected from: mineral salts, such as aluminum hydroxide and aluminum or calcium phosphate gel; oil emulsions and surfactant-based compositions, for example, MF59 (micro-fluidized detergent stabilized by the oil-in-water emulsion), QS21 (purified saponin), AS02 [SBAS2] (oil-in-water emulsion+MPL+QS21), Montanide ISA-51 and ISA-720 (stabilized emulsion "oil in water"); particulate adjuvants, for example, virosomes (unilamellar liposome particles with incorporated influenza hemagglutinin), AS04 ([SBAS4] aluminum salt with MPL), ISCOMS (structured complex of saponins and lipids), polylactide-co-glycolide (PLG); microbial derivatives (natural or synthetic), for example, monophosphoryl lipid A (MPL), Detox, AGP [RC-529] (synthetic acylated monosaccharide), DC_Chol (lipoid immunostimulant), OM-174 (derivative of lipid A), CpG motifs (synthetic oligonucleotides containing immunostimulatory CpG-sequences) modified by LT and CT (genetically modified bacterial toxins to provide a nontoxigenic adjuvant effect); endogenous human immunomodulators, for example, granulocyte-macrophage colony stimulating factor (hGM-CSF) or interleukin-12 (hIL-12) (cytokines that are used both in the form of a protein and in the form of plasmids encoding them), Immudaptin (C3d-tandem region); inert particles such as gold (nano) particles. A priming composition including a DNA plasmid vector may also include granulocyte macrophage-colony stimulating factor (GM-CSF), or a plasmid encoding it or other cytokines, chemokines or growth factors, to act as an adjuvant; beneficial effects are seen using GM-CSF in polypeptide form.

Another object is to provide the dissoluble microneedle drug delivery system, wherein the microneedles of the skin preparation component part i.e., the first inner matrix comprises factors that attract Langerhans cells, such as leukotrienes, galectin-1, interleukin-1b, interleukin-18, tumor necrosis factor-a, as well as adjuvants.

Another object is to provide the dissoluble microneedle drug delivery system wherein the microneedles of the second inner matrix include vaccination/immunization components such as non-viral vectors including lipid-tailed peptides such as lipopeptides, peptides fused to carrier proteins such as KLH either as fusion proteins or by chemical linkage, antigens modified with a targeting tag, C3d or C4b binding protein, whole antigens with adjuvant, and their combinations.

According to certain embodiments the non-viral vectors include inorganic nanoparticles and surfaces that bind or encapsulate DNA, cationic biomolecules, including lipids, polysaccharides, polymers, and dendrimers with electrostatically complex anionic DNA.

According to certain embodiments the microneedles of second inner matrix additionally include stabilizing components that increase the shelf life of vaccine such as polyols: sugars, including mono-, di-, tri-, or oligosaccharides and their corresponding sugar alcohols (trehalose, glucose, sucrose, lactose, fructose, galactose, mannose, maltulose, iso-maltulose, and lactulose, maltose, or dextrose and sugar alcohols of the aforementioned such as mannitol, lactitol, and maltitol).

According to certain embodiments the stabilizing components are in phosphate buffered ethanol solution in combination with methionine or EDTA, or in Tris buffered EDTA in combination with methionine or ethanol (or combinations of methionine and ethanol).

It is an object to provide a dissoluble microneedle drug delivery system, wherein longest microneedles of the outer matrix have lengths ranging between 800 and 1500 micrometers, more preferably, from 850 to 900 micrometers, and the shortest microneedles of this matrix have lengths ranging from 600 to 800 micrometers.

According to certain embodiments the diameter of the longest microneedles ranges between 20 to 50%, preferably about 30% of their length, and the diameter of the shortest microneedles ranges from 30 to 60% of their length.

It is an object to provide a dissoluble microneedle drug delivery, wherein the first and second inner matrices have microneedles of one or more lengths ranging from 40 to 70% of the longest microneedles of the outer matrix.

In certain embodiments the lengths of the microneedles of the first inner matrix are between 400 and 600 micrometers, and the diameter of the microneedles ranges from 50 to 75% of their length.

It is an object of this invention to provide a dissoluble microneedle drug delivery system, wherein the array of microneedles of the first inner matrix comprises microneedles of at least two different lengths, such that longer microneedles are located closer to the outer edges of the matrix while the shorter needles are located close to the center of the matrix.

It is an object of this invention to provide a dissoluble microneedle drug delivery system, wherein a length of the microneedle defined by a vertical axis of the microneedles gradually or stepwise decrease from the outer edge of the outer matrix inwards toward center of the inner matrix, thereby forming a crater or colosseum-like profile shape, respectively.

In some embodiments a length of the microneedles defined by a vertical axis of the microneedles decreases from the outer edge of the outer matrix inwards toward center of the first or the second inner matrix thereby forming a variable profile shape.

According to some embodiments, the dissoluble microneedle delivery system further comprises at least one handle for installation of the inner matrices into the opening window of the outer matrix.

In some embodiments the dissoluble microneedle drug delivery system further comprises a hole (opening) in a center of at least the first inner microneedle matrix for providing liquid components through the hole into a gap between the base of the matrix and surface of the skin. The liquid components may be for hydration of the skin or for improving dissolution of the matrix for example. The second inner microneedle matrix may or may not include a hole in its center.

In some embodiments the first and/or the second inner microneedle matrix has a cuvette (central volume) connected to a channel system within the matrix. The channel system comprises vertical channels in at least some of the needles and the base of the inner matrices have horizontal channels. The vertical needle channels and the horizontal channels are connected via connecting channels allowing or providing entry to enhancing dissolution liquid (edl) components through the horizontal and connecting channels to the vertical needle channels of the microneedles to enhance dissolution of the needles. The enhancing dissolution liquid may be for example a saline solution, distilled water or any liquid that is not harmful to the skin and is approved for cutaneous use. The edl may contain other components as well.

The edl may be distributed into the channel system via a cuvette (also called central volume) located on the upper side of the first and/or second inner matrix.

In some embodiments the dissoluble microneedle drug delivery system further comprises fixation mechanisms with a fixation strip for fixation of the delivery system on a shoulder or a forearm.

In some embodiments the delivery system comprises a bracelet for fixation of the system on an arm.

It is an object of this invention to provide a method of transdermal vaccination of skin, said method comprising: a) attaching an outer matrix of the dissoluble microneedle drug delivery system onto the skin, b) preparing the skin by increasing its hydration of epidermis, and attracting Langerhans cells to vaccination area by attaching the first inner matrix comprising an array of microneedles comprising adjuvant components, c) removing the first inner matrix or allowing the first inner matrix to fully dissolve, and d) attaching the second inner matrix comprising an array of microneedles comprising vaccination/immunization components.

In certain embodiments the method comprises microneedle arrays of the system having a gradient profile having longest microneedles at the edges of the outer matrix and shortest in center area of the inner matrices.

In certain embodiments the method further comprises providing liquid components through a central hole of at least the first inner matrix into a gap between the base of the at least the first inner matrix and surface of the skin.

In some embodiments the method further comprises providing enhancing dilution liquids (edl) via a cuvette connected to a channel network within the base of at least one inner matrix, the channel network comprising vertical needle channels in at least part of the microneedles and horizontal channels within the base, and the vertical and horizontal channels being connected by connecting channels, thereby allowing/providing entry of the edl to the needles and enhancing dissolution of the microneedles.

In certain embodiments the vaccination/immunization components include non-viral vectors including lipid-tailed peptides such as lipopeptides, peptides fused to carrier proteins such as KLH either as fusion proteins or by chemical linkage, antigens modified with a targeting tag, C3d or C4b binding protein, whole antigens with adjuvant, and their combinations.

In certain embodiment the second matrix comprises vaccination/immunization components against COVID 19-disease.

BRIEF DESCRIPTION OF THE DRAWINGS

The following drawings form part of the present specification and are included to further demonstrate certain preferred aspects of the present invention. The invention may be better understood by reference to one or more of these drawings, in combination, with the various embodiments described in the detailed description of the specification presented herein.

FIG. 17A-B shows the system of FIG. 16 from lower side (a) and from side (b).

DETAILED DESCRIPTION OF THE INVENTION

Figure 1:
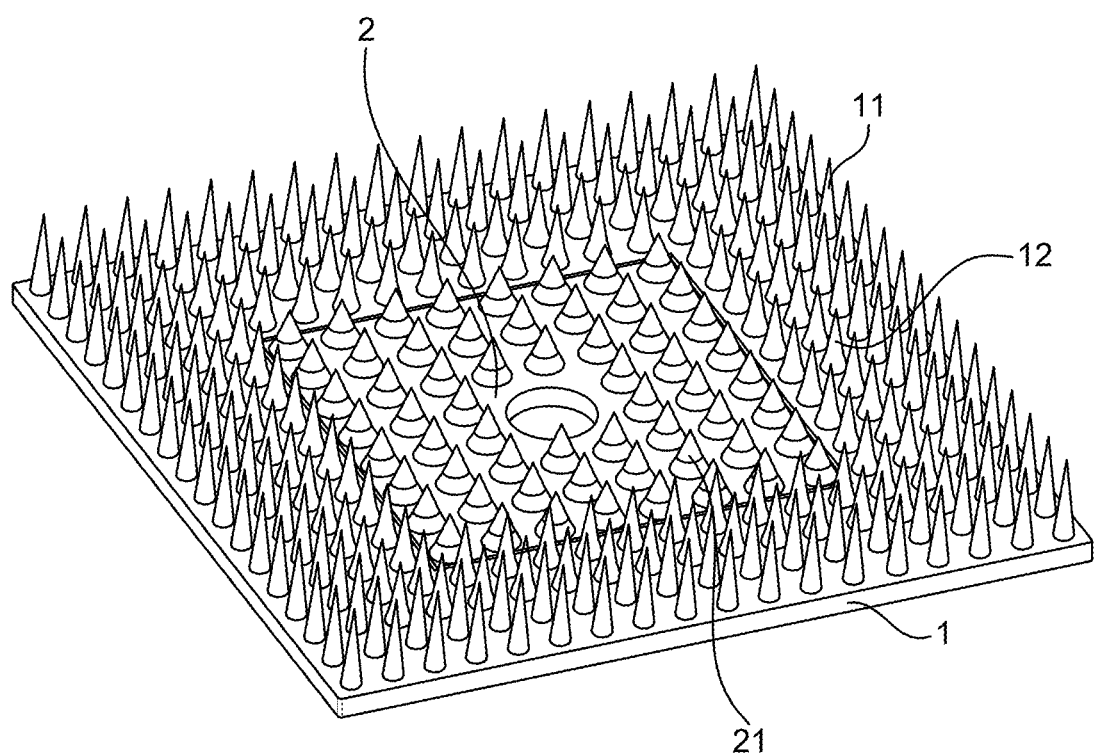
FIG. 1 shows a preferred embodiment of the multifunctional dissoluble microneedle drug delivery system according to this invention. The system includes two sets of matrices, the outer matrix 1, and at least one, fully dissoluble or removable, and replaceable inner matrix 2. In a preferred embodiment there are two inner matrices (a first inner matrix and a second inner matrix) to be used one after another. The outer matrix 1 comprises an array of dissoluble microneedles having profiles as shown in FIG. 5 and used for fixation and for adjuvant administration. The figure shows an embodiment, where two types of the microneedles are integrated onto the outer matrix: longer fixation microneedles 11 and shorter active component carrying microneedles 12. The longer microneedles 11 near the outer edges of the outer matrix are mainly used for fixation of the outer matrix on the skin, although they preferably also include adjuvant. Thus, the outer matrix 1 may also function as a fixation frame. The at least one fully dissoluble or removable, and replaceable first inner matrix 2 may include yet different types of microneedles 21 (the profiles of the microneedles are as shown in FIG. 5). In one procedure, preferably at least two types of the inner matrices 2 (first inner matrix and second inner matrix) are used. The first inner matrix 2 preferably has microneedles for very shallow penetration to prepare the skin to the subsequent main injection with the second inner matrix. The microneedles of the first inner matrix also comprise adjuvant components. The second inner matrix (shown as element number 3 in FIG. 10) includes microneedles specifically prepared for adjuvant and vaccine/immunization injection. According to one embodiment the first inner matrix and the outer matrix are provided as one element and the first inner matrix completely dissolves upon attachment to the skin, after which the second inner matrix can be inserted in its place.

Systemic Immune response in the Skin Cells

The general mechanism of the immune response when antigens such as proteins, polysaccharides, capsids, whole cells, etc. are introduced into the skin includes the following features. The afferent immune link in the skin is represented by two variants of dendritic cells, such as myeloid dendritic cells and Langerhans cells. Both types of dendritic cells absorb foreign material, process it, and after migration to the regional lymph nodes, introduce the antigen to T-lymphocytes.

The efferent component of the lymphoid tissue of the skin is similar to the efferent link of the mucous membranes. The concentration and composition of lymphoid cells in the epithelial (epidermis) and subepithelial (dermis) layers of the skin can significantly differ from each other. The epidermis is dominated by a pool/combination of activated T-lymphocytes (memory cells and effector T-lymphocytes), γδT-cells, CD4+ and CD8+ T-cells. In the dermis, as in the submucosal layer, almost all variants of the cells of the immune system are present, including B lymphocytes and NK cells. The immune response during transdermal administration of antigen activates the Langerhans cells, cross-representing dendritic cells. After absorbing the antigen, dermal dendritic cells and Langerhans cells migrate to the draining lymph nodes, presenting the antigen using major histocompatibility complexes (MHC-I, MHC-II).

Further interaction with T-cell receptors of CD4+ and CD8+ T cells leads to the differentiation of CD4+ T cells into follicular T-helpers and auxiliary T-helpers 1 (Th1), which secrete a large amount of interleukin-2, interferons and tumor necrosis factor. Both subsets of T cells stimulate the proliferation and differentiation of plasma cells secreting antibodies, which in turn cause an IgG2a, IgA and IgM immune response. On the other hand, Langerhans cells induce the differentiation of CD4+ T cells into T-helpers 2 (Th2), as indicated by the secretion of IL-4, IL-5, IL-10 and IL-13, as well as an increase in the level of IgG1 and IgE.

The skin cells are able to initiate a systemic immune response to incoming antigens, which is used in the transdermal administration of vaccines with microneedle applicators. This principle is used in application of the current invention also.

Features of the Functioning of DNA I mRNA Vaccines (or Gene Vaccination)

The essence of gene vaccination is that the protein targets of the immune response are encoded in a specific sequence of DNA or mRNA gene molecules. When introduced into the body, these molecules must "penetrate" through the membrane (penetrate membrane) into a living cell, i.e. pass through the cell membrane (not through phagocytosis, which involves the capture of the substrate and its subsequent destruction by lysosomes).

After penetration into the cell in the cytoplasm (in the case of RNA-vaccine) or in the cell nucleus (in the case of DNA-vaccine), the gene expression process occurs during which the hereditary information from the gene is converted into a functional product, protein (antigen). As soon as these DNA/RNA vaccine products (proteins) enter the intercellular space, the immune response mechanism, the immune response when antigens are introduced, is implemented, namely, the capture of the protein (antigen) by Langerhans cells and transfer them to the lymph nodes and presentation of antigen-specific antigen-specific T-cell populations.

DNA/RNA vaccines typically consist of a bacterial plasmid vector into which a strong viral promoter is inserted, a gene of interest that encodes an antigenic peptide. The gene of interest can encode a complete protein or simply a peptide sequence related to a pathogen, tumor or other agent from which protection is expected. The plasmid can be grown in bacteria, such as, for example, *E. coli,* and then extracted and prepared in a suitable medium, depending on the intended route of administration, before administration to the host. Once introduced into the body, the plasmid must enter into living functioning cells in order to start producing an encoded protein or peptide. The main problem of gene therapy as a whole is the low level of gene expression ("transfection"), due to the fact that a large molecule of plasmid DNA/RNA must be transported through numerous organ, tissue and cell barriers to the nucleus/cytoplasm for efficient expression of antigen. The field of genetic vaccination is still largely limited by the lack of safe and effective gene delivery systems.

To increase the level of transfection, the introduction of viral or bacterial vectors that encode and express a heterogeneous vaccine antigen was initially proposed. However, the introduction of virus DNA can cause unwanted immune responses, oncogenesis, and have unknown long-term effects. The main recombinant viral vectors used for gene delivery are adenovirus, adeno-associated virus (AAV), retrovirus and lentivirus. The advantages of adenovirus are infection of a wide range of human cell types, the ability to infect non-dividing cells and a lower risk of inertial mutagenesis, however, adenovirus expression is short and adenoviruses can cause a severe, even fatal, inflammatory response.

Despite some success has been achieved in the use of viral vectors for gene therapy, there are currently no approved protocols.

Problems with virus delivery systems include immune responses to the vector itself, oncogenicity due to insertional mutagenesis, and the complexity of producing these vectors. Security concerns and restrictions on the use of viral vectors have led to increased interest in non-viral approaches to gene delivery using non-viral materials. Non-viral delivery systems for gene therapy are generally cheaper to manufacture, easy to scale from laboratory to GMP scale, and generally more reliable for long-term storage compared to their viral counterparts. Non-viral vectors for DNA delivery include cationic polymers and lipids, which can form a polyplex with DNA vaccines, effectively protect against enzymatic cleavage and demonstrate better cell transfection efficiency. However, polyplex-based DNA vaccines still require a trained healthcare professional to administer via syringe. As an alternative to improving immunization results, gene delivery systems based on electroporation and a gene gun were used. However, these methods often cause pain or discomfort to the patient and possibly tissue damage, and also require special knowledge to work with the equipment.

Definitions

Unless defined otherwise, all technical and scientific terms used herein have the same meaning as commonly understood by one of ordinary skill in the art to which this invention belongs. Although any materials similar or equivalent to those described herein can also be used in the practice of the present invention, exemplary materials are described for illustrative purposes.

Microneedle as used in this disclosure may be dissoluble, disposable and water-soluble. Microneedles may be responsive to temperature, glucose, pH. They may we swelling and shrinking. The shape and size of the microneedles may be chosen based on the use as described.

Microneedle array or array of microneedles as used in this disclosure means a set of microneedles. A microneedle array comprises a multitude of microneedles which may be similar or different in terms of their length, size, material of which they are made, and/or compounds they include.

First inner matrix and skin preparation component part are used here interchangeably. As used here, the first inner matrix typically comprises a base onto which a set (an array) of dissoluble, microneedles are attached. The base may or may not be fully dissolvable. Similarly, interchangeably are used the terms vaccination/immunization component part and second inner matrix. As used here the second inner matrix typically comprises a base onto which a set (an array) of dissoluble needles are attached. The base may or may not be dissoluble. The terms outer matrix and fixation component part are similarly used interchangeably. The outer matrix typically includes an opening window area which is so dimensioned that an inner matrix fits into the opening window area. Typically, the outer matrix comprises a base onto which a set (an array) of preferably dissoluble microneedles are attached.

As used in this disclosure, the terms "about" or "approximately" are used interchangeably, and are meant to designate any value, which lies preferably within a range of ±5%, more preferably within a range of ±2%, still more preferably, within a range of ±1% of a claimed value. Thus, the term "about" or "approximately" is used to indicate that a value includes the standard deviation of error, which standard deviation, lies preferably within a range of ±5%, more preferably within a range of ±2%, still more preferably, within a range of ±1% of the claimed value.

As used in this disclosure, the term "prophylactic" particularly refers to conferring a complete preemptive protective efficacy against a disease. Especially within the meaning of "prophylactic", and how it relates to the various preferred embodiments of the present invention, it specifically refers to a vaccine composition having a "prophylactic" effect for protecting against a disease that is particularly caused by a virus.

As used in this disclosure, the term "polymer" refers to a high molecular weight organic compound, natural or synthetic, whose structure can be represented by a repeated small unit, the monomer. Synthetic polymers are typically formed by addition or condensation polymerization of monomers. As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves include copolymers. In the context of the preferred embodiments of the present invention, polymers may include the following but not limited to carboxymethylcellulose, or sodium carboxymethylcellulose, or hydroxypropyl methylcellulose, or croscarmellose sodium, or sodium glycolate, or sodium alginate, or sodium lactate, or carrageenan, or pullulan, or polyethylene glycol, or polyvinyl alcohol, or polyvinylpyrrolidone, or pectin, or guar gum, or xanthan gum, as well as mixtures of these substances in various proportions.

As used in this disclosure, the term "administering" refers to an administration of (i) an adjuvant or (ii) a vaccine composition including the following but certainly not limited to a "polynucleotide", "nucleotide", "nucleotide sequence", "nucleic acid", "oligonucleotide", "polypeptide", "peptide", "protein", whole inactivated virus particles or a subunit of an inactivated virus particles or any combination thereof or (iii) immuno-modulatory components, such as but certainly not limited to cytokines, chemokines, growth factors, colony stimulating factors or any combination of (i), (ii) and (iii) transdermal.

As used in this disclosure, the term "chemokine" refers to a class of chemotactic cytokines that signal leukocytes to move in a specific direction. Chemokines are a family of small cytokines or signaling proteins secreted by cells. They can induce directed chemotaxis in nearby responsive cells, and as such, they are chemotactic cytokines. Thus, it refers to movement or orientation of a cell along a chemical concentration gradient either toward or away from a chemical stimulus.

As used in this disclosure, the term "colony stimulating factor" refers to a cytokine responsible for controlling the production of white blood cells. Types include granulocyte colony stimulating factor (G-CSF), macrophage colony stimulating factor (M-CSF), and granulocyte macrophage colony stimulating factor (GM-CSF).

As used in this disclosure, the term "cytokine" refers to small soluble protein substances secreted by cells, which have a variety of immunological effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNF and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of other cytokines. Nonlimiting examples of cytokines include the following IL-1.alpha., IL-.beta., IL-2, IL-3, IL-4, IL-5, IL-6, IL-7, IL-8, IL-9, IL-10, IL-11, IL-12/IL-23 P40, IL13, IL-17, IL-18, TGF-beta., IFN-gamma., GM-CSF, MCP-1 and TNF-alpha.

As used in this disclosure the term, "polynucleotide," "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may include one or more modified nucleotides, such as methylated nucleotides and nucleotide analogs. In some embodiments, modifications to the nucleotide structure are imparted before or after assembly of the polymer. The sequence of nucleotides may be interrupted by non-nucleotide components. The polynucleotide may further be modified after polymerization, such as by conjugation with a labeling component.

As used in this disclosure, the terms "polypeptide," "peptide," and "protein" are used interchangeably herein to refer to polymers of amino acids of any length. In some embodiments, a polypeptide is any protein, peptide, protein fragment, or component thereof. In some embodiments, a polypeptide is a protein naturally occurring in nature or a protein that is ordinarily not found in nature. A polypeptide consisting largely of protein-building amino acids or it is modified to incorporate non-standard amino acids. A polypeptide is modified, typically by the host cell, for example, by adding any number of biochemical functional groups, including phosphorylation, acetylation, acylation, formylation, alkylation, methylation, lipid addition (e.g., palmitoylation, myristoylation, prenylation, etc.) and carbohydrate addition (e.g., N-linked and 0-linked glycosylation, etc.). Polypeptides undergo structural changes in the host cell such as the formation of disulfide bridges or proteolytic cleavage.

As used in this disclosure, the term "adjuvant" refers to any compound that assists or modifies the action of an agent, including but not limited to immunological adjuvants, which increase or diversify the immune response to an antigen. The term also encompasses compounds which when added to an immunogenic or antigen agent, non-specifically enhance an immune response to the agent in the recipient host upon exposure to the mixture. Adjuvants includes compounds that "immunomodulate" the cytokine network, up-regulating the immune response. Concomitant with this immunomodulation there is also a selection of which T-cell, Th1 or Th2, will mount this immune response. Th1 responses will elicit complement fixing antibodies and strong delayed-type hypersensitivity reactions associated with IL-2, IL-12, and gamma-interferon. Induction of CTL response appears to be associated with a TH1 response. Th2 responses are associated with high levels of IgE, and the cytokines IL-4, IL-5, IL-6 and IL-10. The term adjuvants include compounds which, when administered to an individual or tested in vitro, increase the immune response to an antigen in a subject to which the antigen is administered, or enhance certain activities of cells from the immune system. Some antigens are weakly immunogenic when administered alone or are toxic to a subject at concentrations that evoke useful immune responses in a subject. An adjuvant can enhance the immune response of the subject to the antigen by making the antigen more strongly immunogenic. The adjuvant effect can also result in the ability to administer a lower dose of antigen to achieve a useful immune response in a subject.

As used in this disclosure, the term "antigen" refers to a molecule which contains one or more epitopes capable of stimulating a host's immune system to make a cellular antigen-specific immune response when the antigen is presented in accordance with the present invention, or a humoral antibody response. An antigen may be capable of eliciting a cellular or humoral response by itself or when present in combination with another molecule. Normally, an epitope will include between about 3-15, preferably about 5-15, and more preferably about 7-15 amino acids. Epitopes of a given protein can be identified using any number of epitope mapping techniques, well known in the art. See, e.g., *Epitope Mapping Protocols in Methods in Molecular Biology*, Vol. 66 (Glenn E. Morris, Ed., 1996) Humana Press, Totowa, N.J. For example, linear epitopes may be determined by e.g., conarrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708871 and Geysen et al. (1984) *Proc. Natl. Acad. Sci. USA* 81:3998-4002; Geysen et al. (1986) *Molac. Immunol.* 23:709-715. Similarly, conformational epitopes are readily identified by determining spatial conformation of amino acids such as by, e.g., x-ray crystallography and 2-dimensional nuclear magnetic resonance. See. e.g., *Epitope Mapping Protocols*, supra.

The term "antigen" as used herein denotes both subunit antigens, i.e., antigens which are separate and discrete from a whole organism, with which, the antigen is associated in nature, as well as killed, attenuated or inactivated bacteria, viruses, parasites or other microbes. Similarly, an oligonucleotide or polynucleotide which expresses a therapeutic or immunogenic protein, or antigenic determinant in vivo, such as in gene therapy and nucleic acid immunization applications, is also included in the definition of antigen herein. Further, for purposes of the present invention, antigens can be derived from any of several known viruses, bacteria, parasites and fungi, as well as any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

As used in this disclosure, the term "immunological response" or "immune response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of endogenous cytokines, chemokines and other such molecules produced by activated T-cells and/or other white blood cells, including those derived from CD4+ and CD8+ T-cells.

As used in this disclosure, the term "inhibit" and its various grammatical forms, including, but not limited to, "inhibiting" or "inhibition", are used herein to refer to reducing the amount or rate of a process, to stopping the process entirely, or to decreasing, limiting, or blocking the action or function thereof. Inhibition can include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

As used in this disclosure, the term "inhibitor" refers to a second molecule that binds to a first molecule thereby decreasing the first molecule's activity.

As used herein this disclosure, the term "predetermined" is related to a number greater than zero that has been set during the optimization of the embodiments of the described invention. As such, it can be used in the context such as a "predetermined time" in accordance with the preferred embodiments of the invention.

As used in this disclosure, the term "reduced" or "to reduce" refers to a diminution, a decrease, an attenuation or abatement of the degree, intensity, extent, size, amount, density or number.

As used in this disclosure, the term "similar" is used interchangeably with the terms analogous, comparable, or resembling, meaning having traits or characteristics in common.

As used in this disclosure, the term "human", "subject", "individual" or "patient" are used interchangeably to refer to a member of an animal species of mammalian origin, preferably humans.

When using terms characterized by but not limited to "substantial", "substantially", "essential" or "essentially" herein, it is intended that the feature, which is described by these terms is present in an amount or has an impact, which provides for a technical effect with relevance for the exercise of the presently claimed invention.

As used in this disclosure, the terms "includes," "comprising," "including," "having" and their conjugates mean "including but not limited to." Terms and phrases used in this application, and variations thereof, unless otherwise expressly stated, should be construed as open ended as opposed to limiting. As examples of the foregoing, the term "including" should be read as meaning "including, without limitation" or the like. The term "example" is used to provide exemplary instances of the item in discussion, not an exhaustive or limiting list thereof. Adjectives such as, e.g., "conventional," "traditional," "known" and terms of similar meaning should not be construed as limiting the item described to a given time period, or to an item available as of a given time. But instead these terms should be read to encompass conventional, traditional, normal, or standard technologies that may be available, known now, or at any time in the future.

Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. The presence of broadening words and phrases such as, "one or more," "at least," "but not limited to," or other like phrases in some instances shall not be read to mean that the narrower case is intended or required in instances, where such broadening phrases may be absent.

It will be readily understood by one of ordinary skill in the relevant art that the present invention has broad utility and application.

Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method, product or use of the invention, and vice versa.

Detailed Description

The disclosed microneedle immunotherapeutic system is a multi-component system and the system, and its various embodiments are now described with reference to the figures.

The system includes component elements that have different functions. The system includes at least a fixation component part, a skin preparation component part, and a vaccine component part. The system may additionally have further components, such as inflammation prevention part or soothing component part.

The fixation component part has a function of attaching the system onto the skin. The fixation component part preferably has a multitude of microneedles that have a length such that they attach the fixation component onto the skin. The fixation microneedles of the fixation component part are preferably dissolvable by nature. The microneedles of the fixation component part may or may not include chemical or medical components. The fixation component part may instead or additionally have other fixing features, such as adhesive surfaces.

The skin preparation component part is removable and replaceable and has a function to prepare the skin to receive the vaccine/immunization provided in the vaccine component part. The skin preparation part is applied onto the skin before the vaccine component part. According to a certain embodiment one skin preparation component part may be replaced by another skin preparation component part. The skin preparation part includes a multitude of microneedles.

The microneedles of the skin preparation component part may be of different sizes (length and diameter) and different compounds may be delivered through them. The microneedles of the skin preparation component part may be hollow. According to a preferred embodiment the microneedles of the skin preparation component part are dissoluble.

The vaccine component part is removable and replaceable and has a function to transdermally administer the vaccine. The vaccine component part is applied on the skin after one or more skin preparation component parts are applied and removed, respectively. According to certain embodiments the vaccine component part can be applied without first applying the skin preparation component part. According to certain embodiments more than one vaccine component part may be applied one after another. According to a preferred embodiment the microneedles of the vaccination part are dissoluble.

According to certain embodiments a soothing or inflammation preventing component part may be applied after the vaccine component part.

Now referring to FIG. 1, the system comprises an adjuvant/fixation component part that is a microneedle matrix (outer matrix 1). A skin preparation component part or vaccination/immunization component part is shown as inner matrix 2. The inner matrix fits into the into an opening window area, In FIG. 6 for example it is shown how the outer matrix 1 has a window opening area 15 into which the inner matrix 2 fits. The fixation component part has a multitude of microneedles 11 on its lower side. This fixation component part is attached to the skin via the microneedles 11 that are arranged on the base of the fixation component part. The matrices can be integrated on patches for more practical use.

Figure 15:
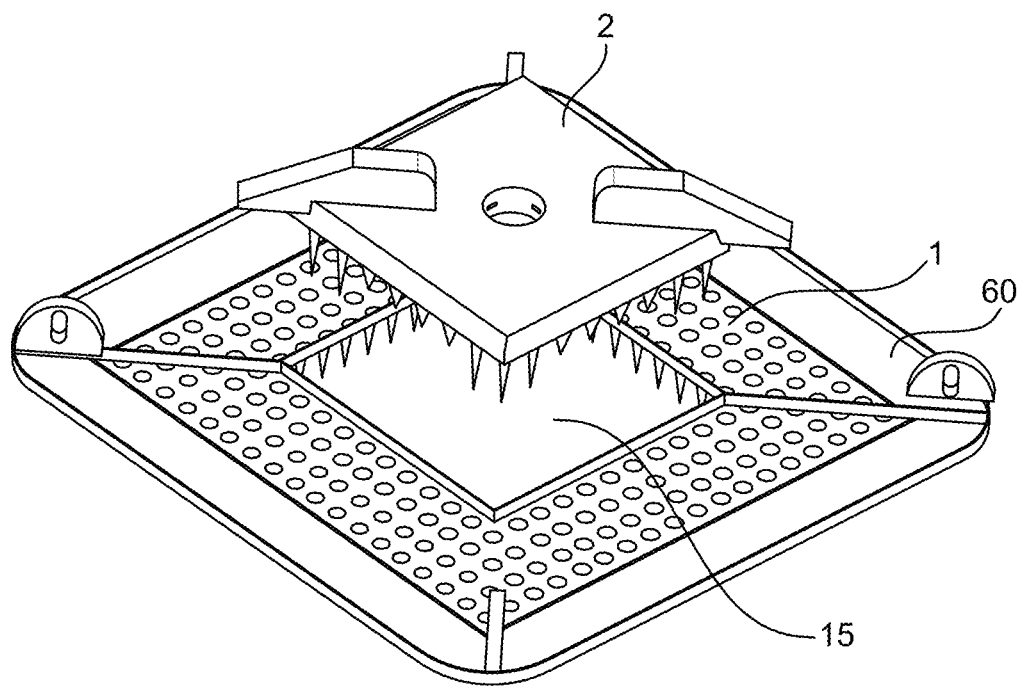
FIG. 15 shows an embodiment of the system where the outer matrix 1 is integrated into the frame 60. The inner matrix 2 is shown separated from the outer matrix 1 here. The opening window area 15 of the outer matrix is visible here.
Figure 16:
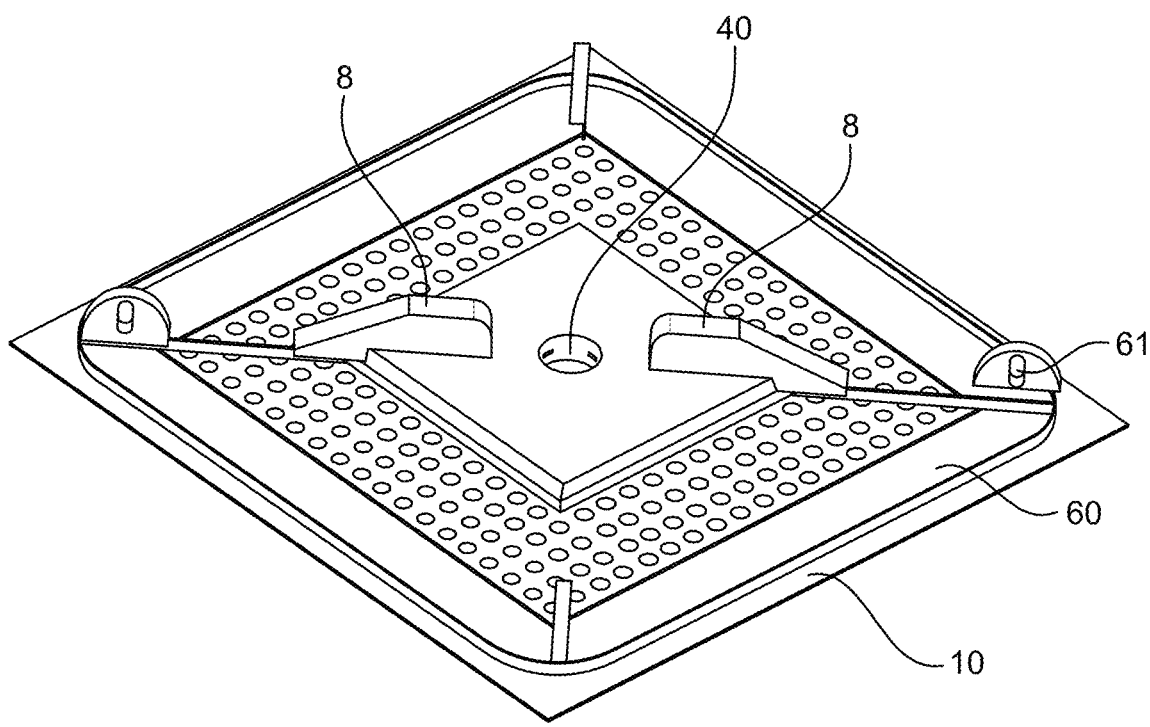
FIG. 16 shows an embodiment of the system where the outer matrix 1 is integrated into the frame 60. The inner matrix 2 and the outer matrix 1 are in the setting position. The inner matrix is fixed to the opening window area of the outer matrix with the handles 8. The frame 60 includes fixation mechanisms 61.

According to certain embodiments there is an additional frame 60, such as shown in FIGS. 15 and 16. Such fixation unit is a frame into which the fixation component part (outer matrix 1) fits. The frame may include adhesive material to further support it on the skin. According to certain embodiments the fixation component part (outer matrix 1) and the frame 60 are one component placed on the skin simultaneously. According to another embodiment the frame 60 may be first attached to the skin and the fixation component part (outer matrix 1) is inserted into the frame separately.

Figure 6:
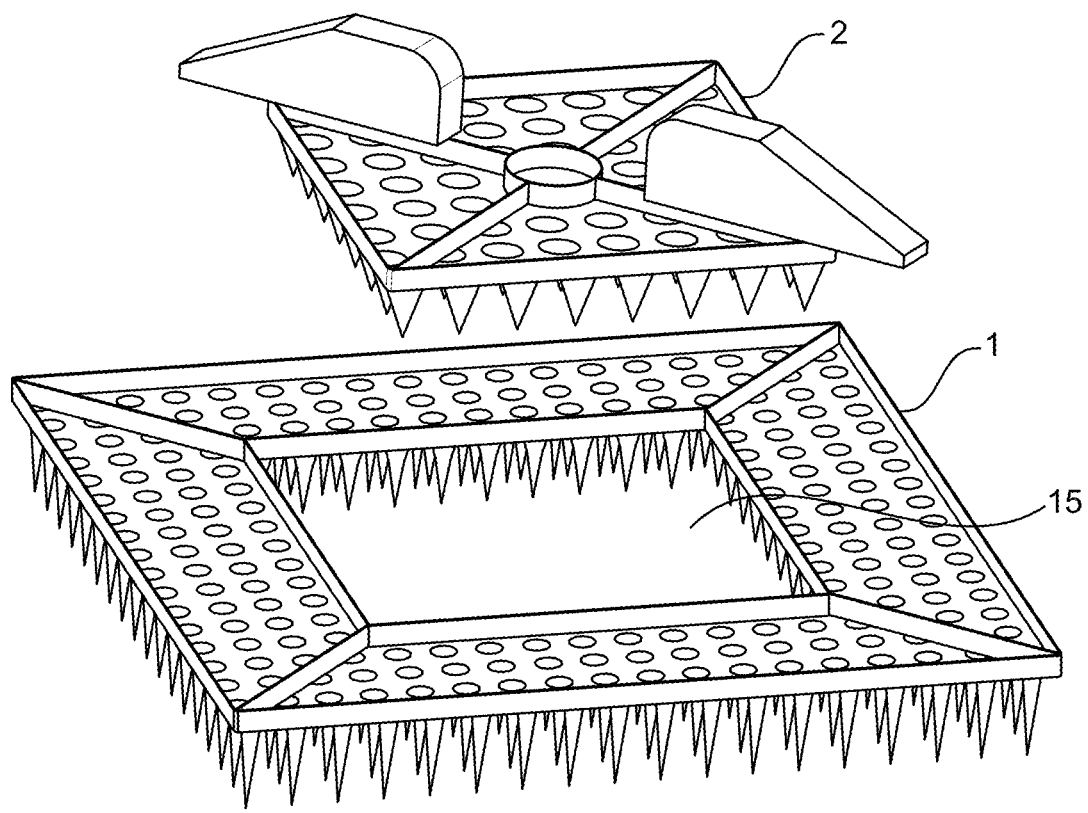
FIG. 6 shows a perspective view of the multifunctional dissoluble microneedle drug delivery system is shown, such that the inner matrix 2 with handles attached thereto is separated from the outer matrix 1 having an opening window area 15.
Figure 7:
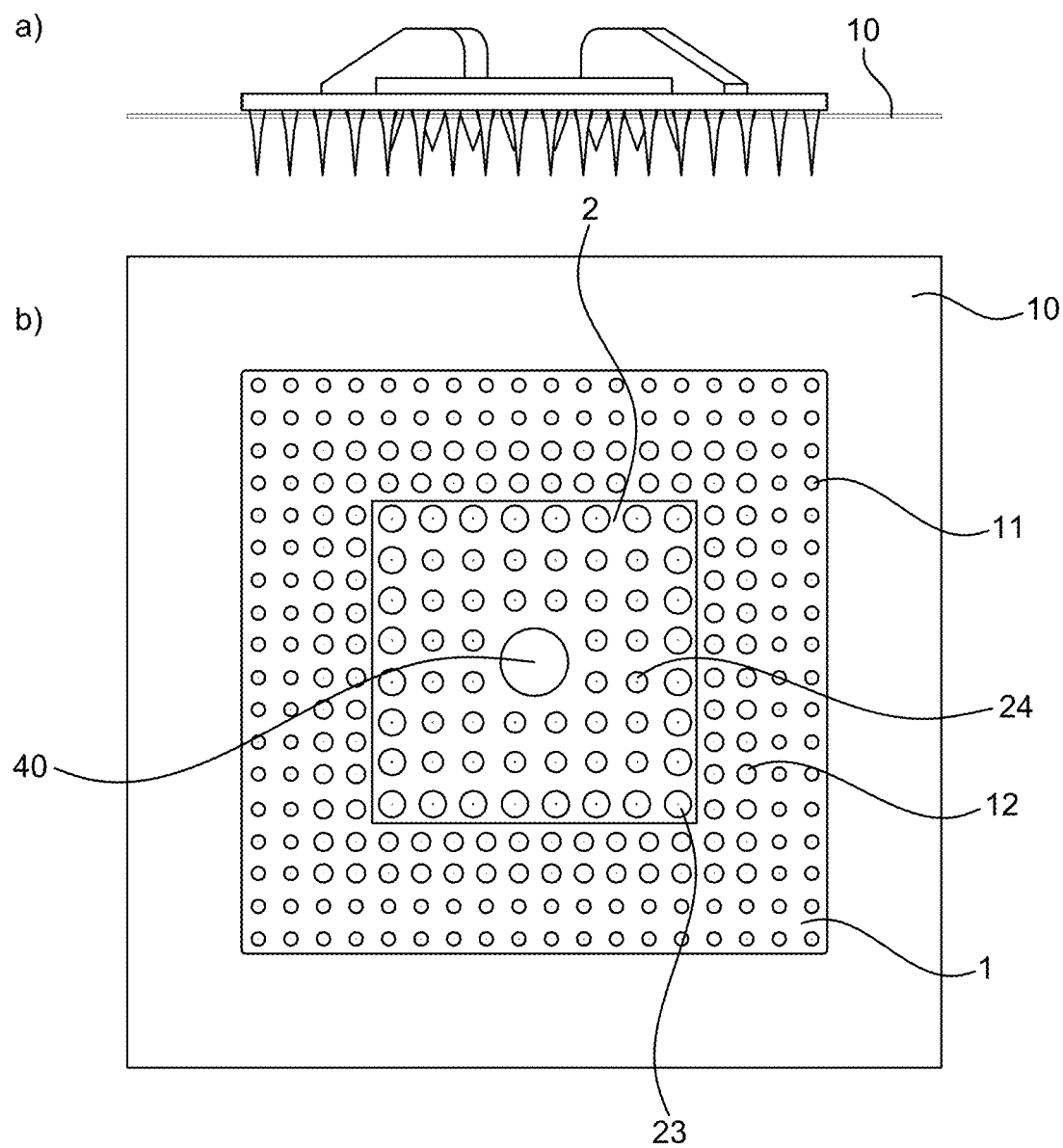
FIG. 7A-B show a typical map of the microneedles of the multifunctional dissoluble microneedle drug delivery system. a) shows a cross-section of the system injected into the skin 10. B) shows the bottom (microneedle side) of the system. The outer matrix 1 includes microneedles of types 11 and 12, and the inner matrix 2 includes microneedles of type 23 and 24. The inner matrix 2 has a central opening (hole) 40 in the middle.
Figure 8:
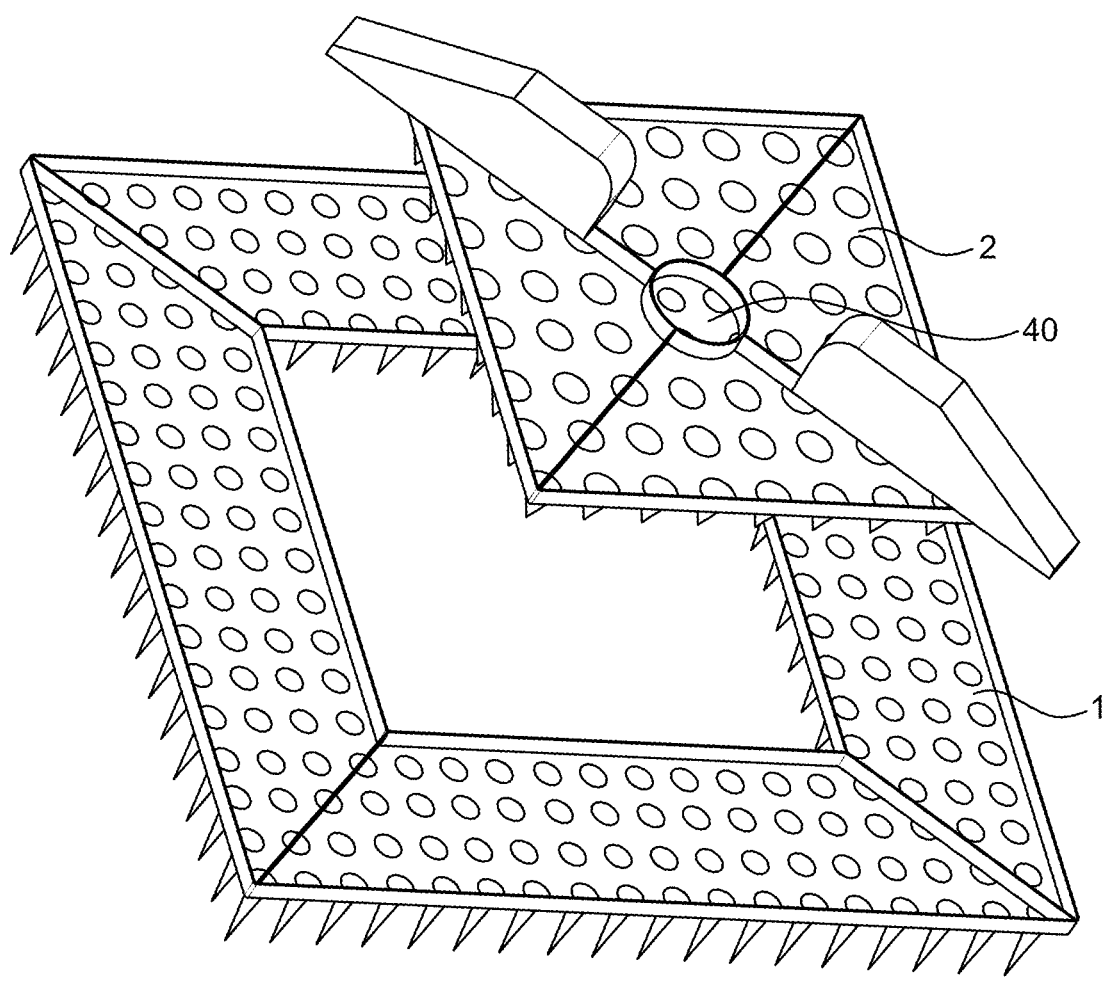
FIG. 8 shows typical relative sizes of the outer matrix 1 and the inner matrix 2 of the system. In this embodiment the inner matrix 2 is equipped with at least one opening (hole) with a cuvette (central volume) 40*a* in the center of the inner matrix 2 to provide means for measuring a volume of a liquid component (edl) to be added. The liquid component can penetrate into the gap (numeral 20 in FIG. 3) between the skin and the bottom surface of the bases of the system for improving mechanical contact, and/or the liquid may enter the channel system as is shown in FIGS. 11-13.
Figure 9:
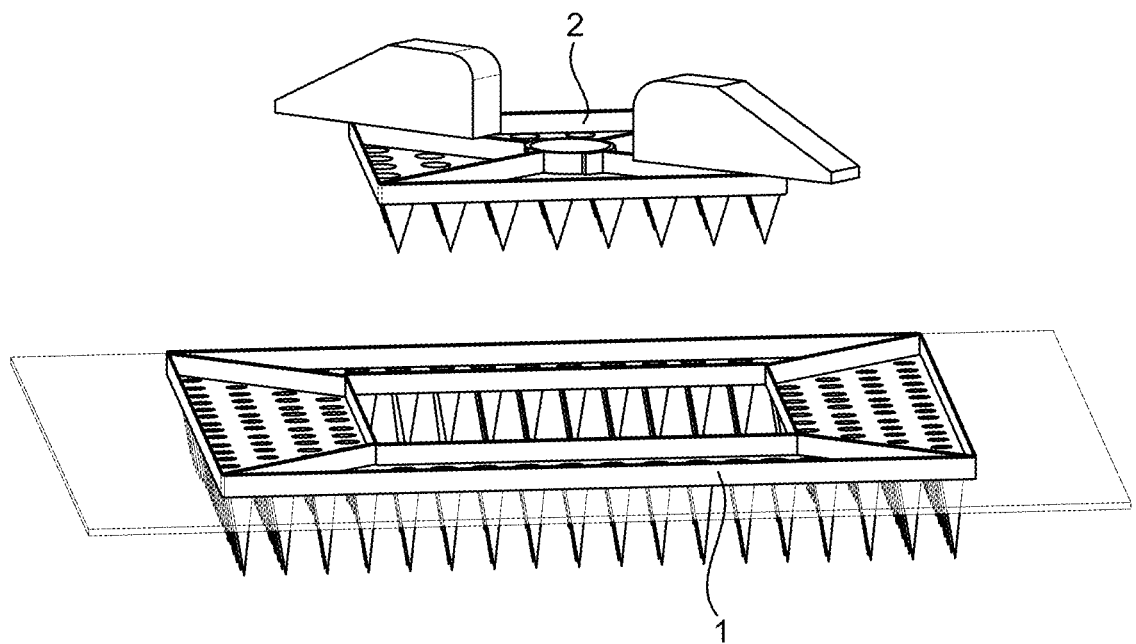
FIG. 9 illustrates the system of FIG. 8 from a different angle.
Figure 20:
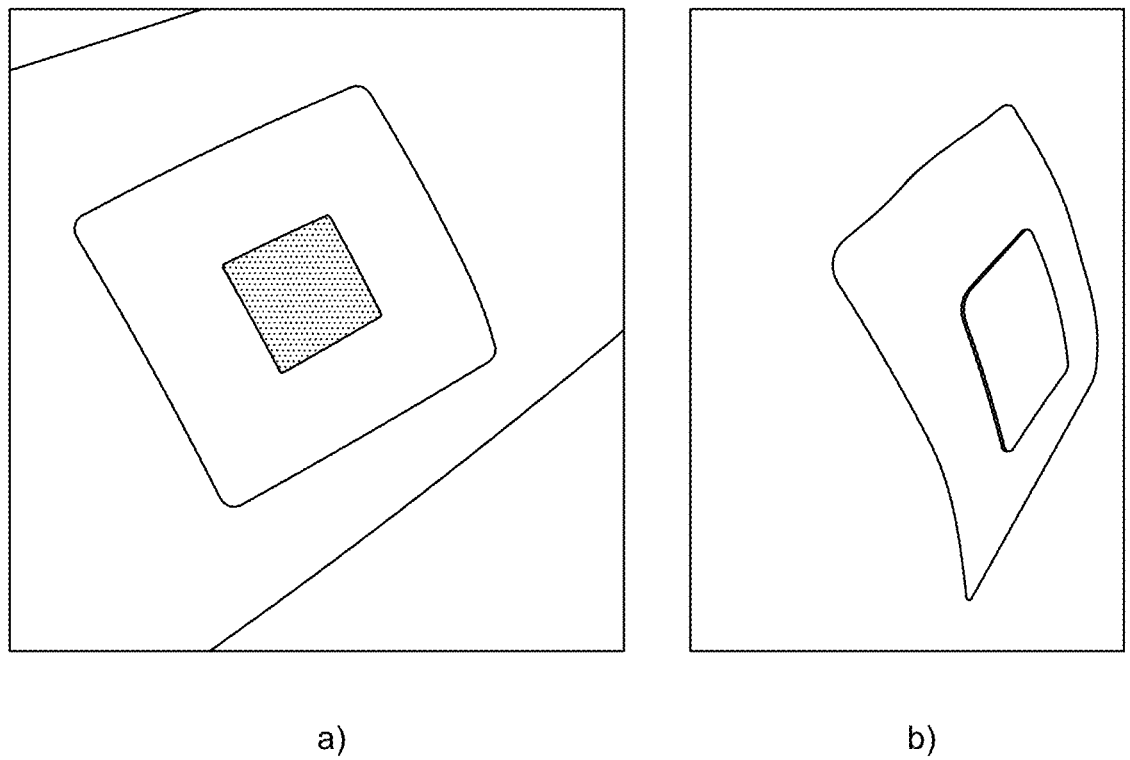
FIG. 20A-B illustrates the dissoluble microneedle drug delivery system applied on human skin. In a) the outer matrix applied on the skin is shown with empty window opening area. b) shows an inner matrix applied in the window opening.

The inner matrix 2 shown FIG. 1, may be a skin preparation component part or a vaccine component part or any additional parts such as inflammation preventing part or soothing component part. The inner matrix 2 is removable and replaceable. Thus, one inner matrix is replaced with another one. FIG. 6 and FIG. 20 for example show inserting an inner matrix 2 into the outer matrix 1. FIG. 10a-e shows inserting one inner matrix 2 into the outer matrix 1, then removing it and replacing it within another inner matrix 3. The system according to this invention is thus used in at least two stages: The fixation component part and the preparation component are applied first onto the skin and the vaccine component thereafter. The first inner matrix being the preparation component part is generally allowed to be on the skin for a time period long enough to allow the microneedles of the matrix to dissolve. This time period depends on the chemical structure of the needles. According to certain embodiments the preparation component part (first inner matrix) remains attached on the skin 10 to 30 minutes, preferably 15 to 20 minutes. Similarly, the vaccination matrix is allowed to be on the skin for a time period long enough to allow the microneedles dissolve.

Figure 2:
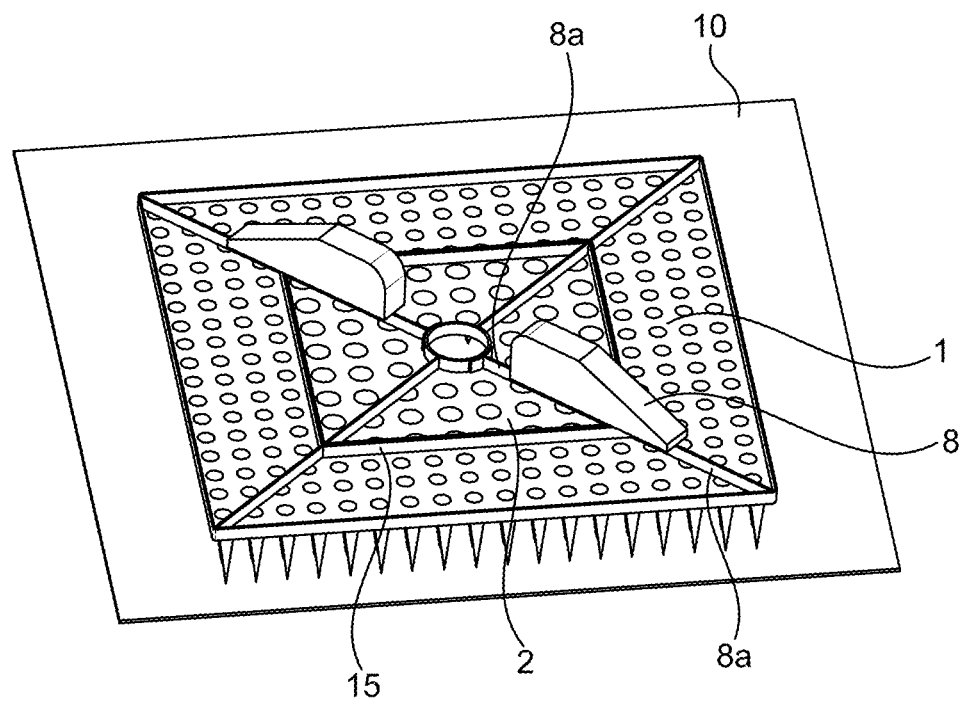
FIG. 2 shows the multifunctional dissoluble microneedle drug delivery system applied on the skin. The figure shows the skin 10, an outer matrix 1, and an inner matrix 2. The system is equipped with handles 8 for installation of the inner matrix 2 into the opening window area 15 of the outer matrix. The upper surfaces of the matrices have grooves 8*a*, along which the handles can be moved.
Figure 3:
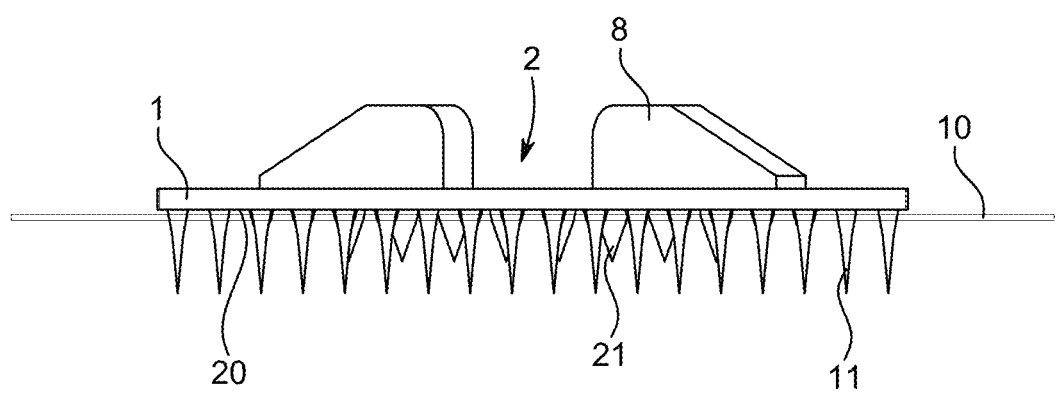
FIG. 3 shows a side view of the multifunctional dissoluble microneedle drug delivery system attached to the skin. The figure shows the skin 10, the outer matrix 1 having fixation microneedles 11. The figure also shows the needles 21 of the inner matrix 2. The system is equipped with handles 8. As a small gap 20 remains in between the matrices and the skin which is depictured in the figure.

As is shown in FIG. 2 for example, the system may have handles 8 on its top side. The handles 8 may be arranged, such that they can be moved on top of the device to lock the inner matrix 2 into the window opening area of the outer matrix 2. The outer surface of the outer matrix and the inner matrix may have grooves 8a along which the handles 8 can move when the grooves coincide, thus locking the inner matrix into the outer matrix.

The system according to this invention comprises a multitude of microneedles of different sizes depending on their function. Various microneedle arrays and structures are described now in more details.

Figure 4:
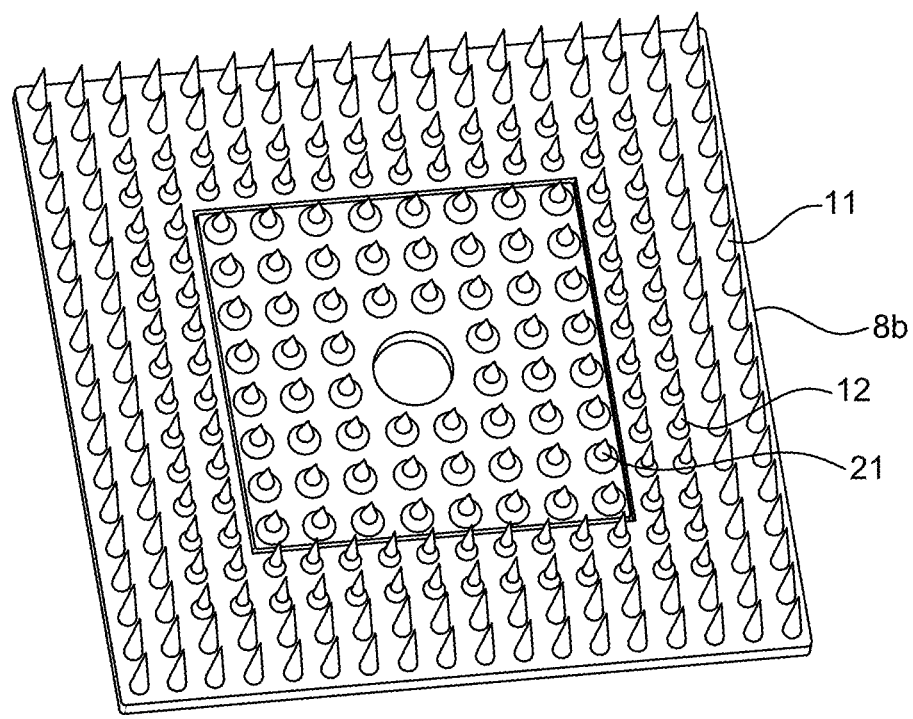
FIG. 4 is a perspective view of the multifunctional dissoluble microneedle drug delivery system revealing typical sizes of the bases of the microneedles. The fixation microneedles 11 are usually the longest ones and have smaller base diameter than other microneedles. They are mainly used for fixation of the system onto the skin. Other microneedles 12, 21 are usually shorter having bigger base sizes. Outer edge of the outer matrix is indicated by numeral 8*b*.

The fixation component part (outer matrix 1) comprises at least two sets of microneedles on its lower side (base) that is attached toward the skin. As is shown for example in FIG. 4, there is one set of microneedles 11 along the outer edges 8b of the fixation component part. Another set of microneedles 12 is shown along the inner edges of the fixation component part (outer matrix 1). According to one preferred embodiment the microneedles 11 closest to the outer edges are the longest ones. According to certain embodiments the fixation component part (outer matrix 1) has one row of longest microneedles; according to certain embodiments the fixation component part (outer matrix 1) has several rows of the longest microneedles 11. According to certain embodiments the length of the microneedles gradually decreases from the outer edge toward the inner edge of the fixation component part (outer matrix 1). FIG. 5a-c shows various profiles of the microneedle arrays. At least the longest set of microneedles 11 has a function to fix the fixation component part onto the skin.

According to one preferred embodiment the fixation microneedles 11 have lengths ranging between 600 and 1500 micrometers, more preferably, from 850 to 900 micrometers (referenced as 100% percent for comparison) and the diameter of the bases ranging between 20% to 50% of the length, preferably, 250-300 micrometers (size/length=30%) arranged near and around the outer edge of the fixation component part (outer matrix 1).

The problem of previously known matrices of microneedles having equal lengths is that due to skin deformation during application of the matrix, the microneedles of the central part of the matrix penetrate at smaller depth. Therefore, introducing the fixation component part (outer matrix 1) which function is fixation of the frame of the matrix on the skin improves injection of the subsequent components administered via the inner matrix 2.

The second set of the microneedles 12 (shown e.g., in FIG. 1) of the fixation component part (outer matrix 1) is equipped with microneedles having length about 70% to 100% of the length of microneedles 11. Preferably, the length of the microneedles 12 varies between 650 to 800 micrometers and base size between 300 and 400 micrometers (size/length between 30 and 60%). This set is placed closer to the inner edge of the fixation component part. According to certain embodiments there can be additional sets of microneedles in-between these two main sets.

Figure 5:
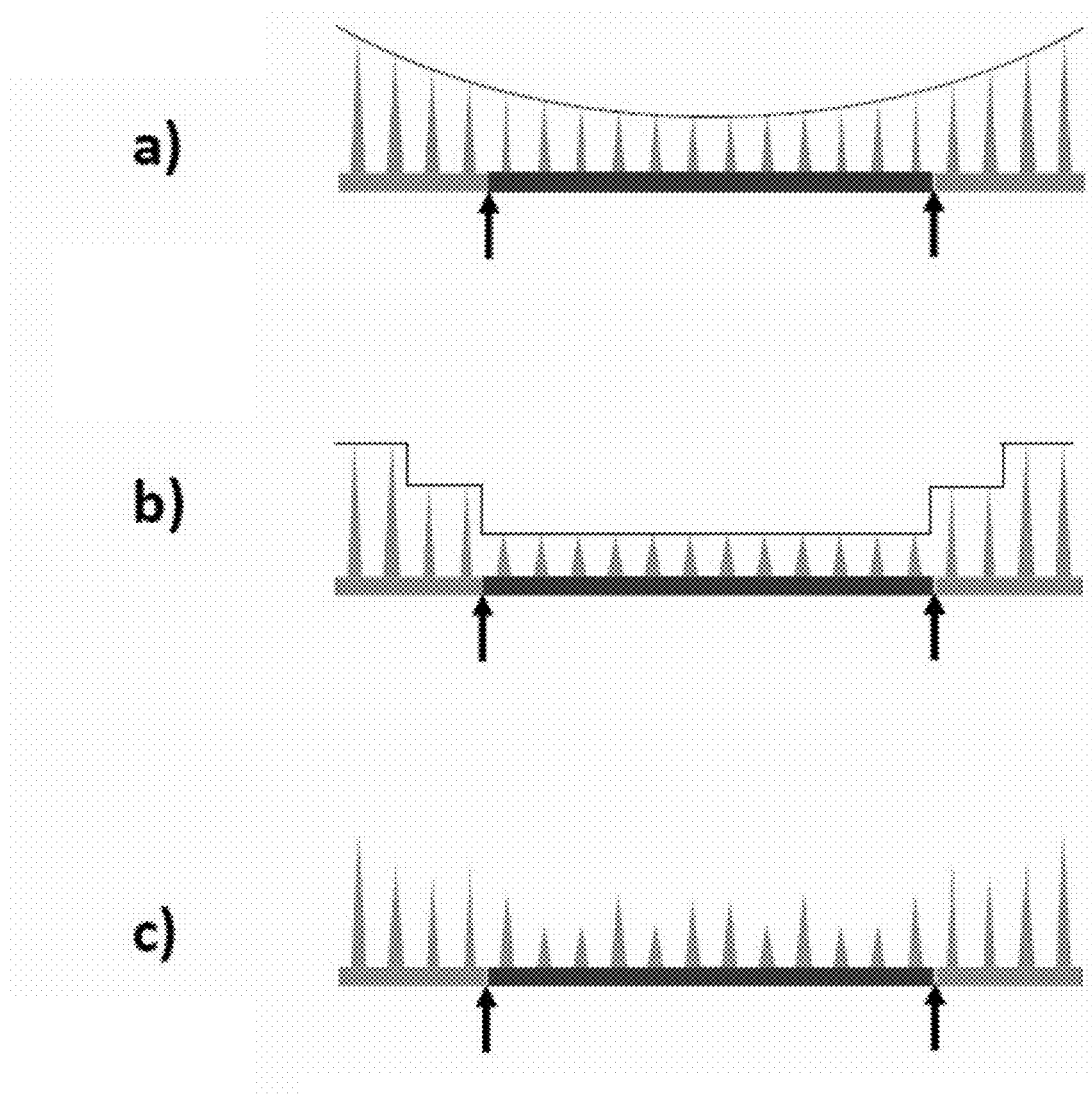
FIG. 5A-C show different profiles of the microneedles from the outer edges towards the center of the dissoluble microneedle drug delivery system. The profile a) has a crater-shape, b) a colosseum-shape and c) a variable profile. The inner edge of the outer matrix/outer edge of the inner matrix is visible in the figures (indicated by arrows).

Various embodiments of the microneedle arrays are shown in FIG. 5. In FIG. 5a, an embodiment is shown where the fixation component part (outer matrix 1) has one row of longest microneedles closest to its outer edge. Shortest microneedles of the fixation component part are arranged closest to the inner edge. Two rows of medium long microneedles are arranged in rows in between the longest and the shortest microneedles. The length of the microneedles decreases gradually toward the inner edge of the fixation component part.

In FIG. 5b an embodiment is shown where there are two rows of longest microneedles next to the outer edge, and two rows of shortest needles next to the inner edge. The length of the microneedles decreases stepwise toward the inner edge of the fixation component part.

In FIG. 5c and embodiment is shown where there is one row of longest microneedles next to the outer edge of the outer matrix and three rows of shortest microneedles arranged next to the inner edge of the outer matrix 1.

According to a preferred embodiment the fixation component part (outer matrix 1) having at least two different sets of microneedles 11, 12 remains attached on the skin during the entire injection procedure. By injection procedure it is meant the at least two step procedure including attaching at least two inner matrices 2 one after another inside the opening window of the outer matrix 1.

The second component of the system of this invention is at least two subsequent, and optionally more than two subsequent inner matrices inside the opening window 15 of the outer matrix 1. The inner matrices are removable and exchangeable, and they can be replaced with another inner matrices during the injection procedure. According to one preferred embodiment the first inner matrix completely dissolves, and second inner matrix is applied in its place.

The first inner matrix 2 is a skin preparation component part. This matrix has size of the opening window area 15 of the fixation component part. As shown for example in FIG. 4, the skin preparation component part (inner matrix 2) has an array of microneedles 21 on its lower side (base) to penetrate into the skin once the skin preparation component part is placed into the opening window 15. According to a preferred embodiment these microneedles are shorter than any of the microneedles of the fixation component part. According to one preferred embodiment these microneedles are the shortest of any microneedles of this system. Their function of the skin preparation matrix is preparation of the top skin layer to the application of subsequent vaccination/immunization component part. The microneedles 21 of the skin preparation component part (inner matrix 2) have lengths in the range of 40% to 70% of the length of the longest fixation microneedles 11, preferably the length is between 400 to 600 micrometers and base diameter between 300 to 400 micrometers i.e. 50-75% of the length of the microneedles.

According to this invention, a major function of the skin preparation component part is to attract dendritic cells, including Langerhans cells to the vaccination sites. In order to achieve this goal, the microneedles of the skin preparation component part may initiate a pro-inflammatory reaction when piercing the skin. Alternatively, or additionally the microneedles of the skin preparation component part comprise factors that attract Langerhans cells. Such factors may be leukotrienes, galectin-1, interleukin-1b, interleukin-18, tumor necrosis factor-α, as well as adjuvants.

The preferable adjuvants may be selected from: mineral salts, such as aluminum hydroxide and aluminum or calcium phosphate gel; oil emulsions and surfactant-based compositions, for example, MF59 (micro-fluidized detergent stabilized by the oil-in-water emulsion), QS21 (purified saponin), AS02 [SBAS2] (oil-in-water emulsion+MPL+QS21), Montanide ISA-51 and ISA-720 (stabilized emulsion "oil in water"); particulate adjuvants, for example, virosomes (unilamellar liposome particles with incorporated influenza hemagglutinin), AS04 ([SBAS4] aluminum salt with MPL), ISCOMS (structured complex of saponins and lipids), polylactide-co-glycolide (PLG); microbial derivatives (natural or synthetic), for example, monophosphoryl lipid A (MPL), Detox (MPL+cell wall structures of M. Phlei), AGP [RC-529] (synthetic acylated monosaccharide), DC_Chol (lipoid immunostimulant), OM-174 (derivative of lipid A), CpG motifs (synthetic oligonucleotides containing immunostimulatory CpG-sequences) modified by LT and CT (genetically modified bacterial toxins to provide a non-toxigenic adjuvant effect); endogenous human immuno-modulators, for example, granulocyte-macrophage colony stimulating factor (hGM-CSF) or interleukin-12 (hIL-12) (cytokines that are used both in the form of a protein and in the form of plasmids encoding them), Immudaptin (C3d-tandem region); inert particles such as gold (nano) particles. A priming composition including a DNA plasmid vector may also include granulocyte macrophage-colony stimulating factor (GM-CSF), or a plasmid encoding it or other cytokines, chemokines or growth factors, to act as an adjuvant; beneficial effects are seen using GM-CSF in polypeptide form.

When initiating a pro-inflammatory reaction and introduction of adjuvants, the Langerhans cells located in the epidermis capture antigens, inflammatory factors mature and the Langerhans cells move to the lymphatic vessels, according to various estimates, it takes 2-4 hours. During this time, Langerhans cell precursors take the place of "departed" cells and begin their development cycle.

Figure 10:
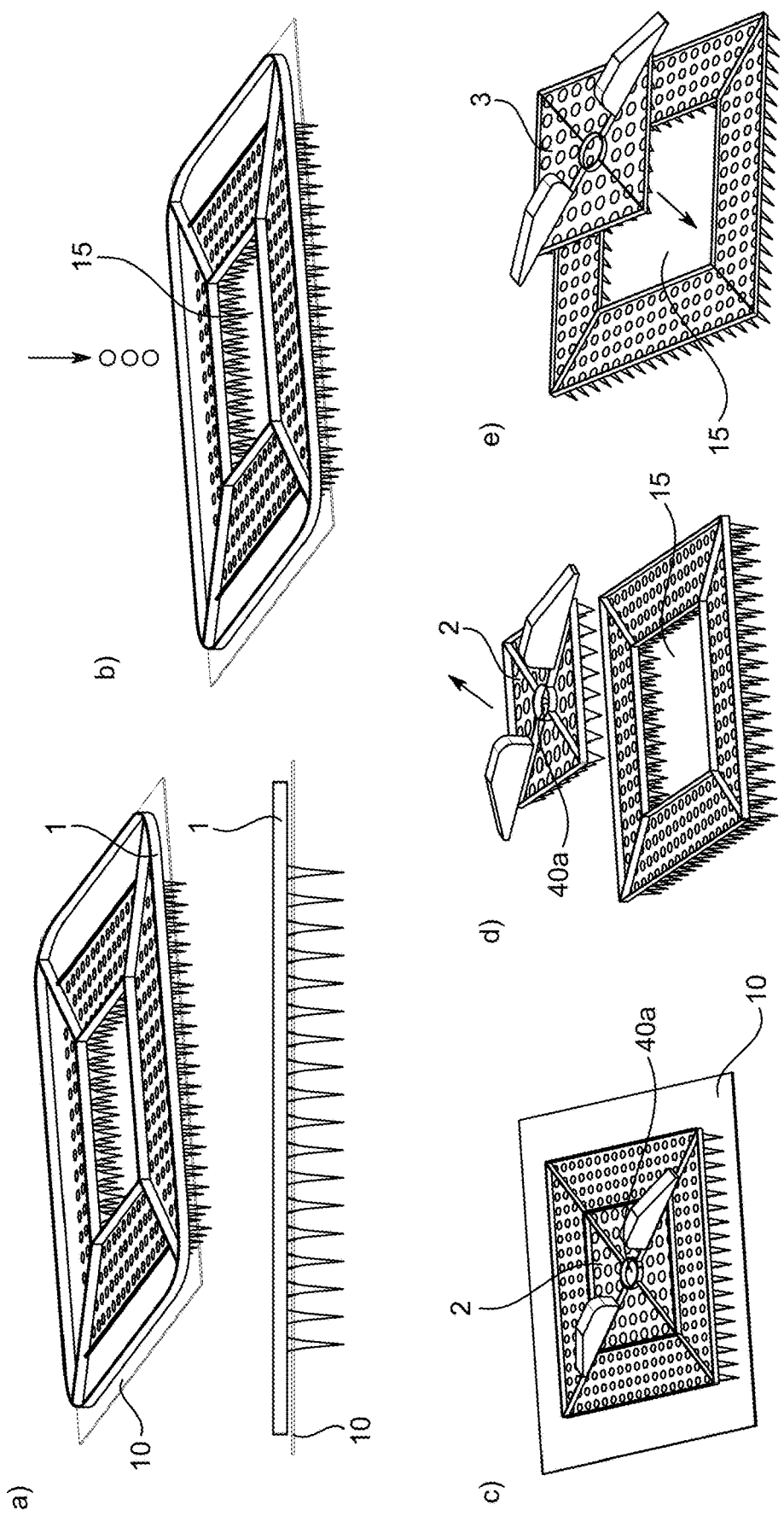
FIG. 10A-E shows the principle of use of the multifunctional dissoluble microneedle drug delivery system. The system is applied in multiple steps. Step 1: application of the outer matrix 1 on the skin 10 is shown in a). Step 2: application of a first inner matrix 2 into the opening window area 15 of the outer matrix 1 is shown in b). This stage is preparing the skin for subsequent injection. After application of the matrix into the opening window area a tiny gap remains between the matrix and the skin. This gap can be used for delivering liquid on the skin added in the following step. The gap is shown as element 20 in FIG. 3. Step 3: adding a liquid component through the central hole 40 of the inner matrix 2 is shown in c). The liquid component penetrates into the gap (numeral 20 in FIG. 3) between the skin surface and the bottom surfaces of the bases of the matrices. This improves the mechanical contact by removing air from the gap. After dissolution of the microneedles of the first inner matrix 2, the first inner matrix 2 is removed from the system, shown in d). Replacement of the first inner matrix 2 with preferably a different type of a second inner matrix 3 for main vaccination/immunization is shown in e). The second inner matrix 3 has preferably the same size as the first matrix 2, so that it fits in the same opening window area 15 of the outer matrix 1. After the application of the second inner matrix 3, there is some lag time before the active components are dissolved in the skin. Once the components are dissolved into the skin, the whole system is removed from the skin. The injection procedure is completed. In an embodiment where the outer matrix and the first inner matrix come as one element, the steps 1 and 2 are completed simultaneously.

After use of the skin preparation component part, it is replaced with another inner matrix, namely vaccine matrix (second inner matrix). FIG. 10d shows removal of a first inner matrix 2 (skin preparation component part) and FIG. 10e shows inserting the second inner matrix 3 i.e. vaccination/immunization matrix instead. The function of the second inner matrix is to perform the main vaccination into the skin.

The vaccine/immunization composition of the vaccination/immunization matrix (second inner matrix) may include a subunit of a pathogen, or a peptide or polypeptide derivable therefrom including one or more antigenic epitope(s). The vaccine/immunization composition may include a nucleotide sequence, such as an RNA or DNA sequence capable of encoding a peptide or polypeptide including one or more antigenic epitope(s).

The microneedles of the vaccination/immunization matrix may include RNA or DNA stabilizing agents that inhibit the degradative effects of free radicals (one or both of a metal ion chelator and a free radical scavenger) or such as inositol hexaphosphate, tripolyphosphate, succinic and malic acid, ethylenediamine tetra acetic acid (EDTA), tris (hydroxymethyl) amino methane (TRIS), Desferal, diethylenetriamine-pentaacetic acid (DTPA) and ethylenediamindihydroxyphenylacetic acid (EDDHA), ethanol, methionine or glutathione, antioxidant enzymes and other antioxidant components.

Also, microneedles of the vaccination/immunization matrix may include stabilizing components that increase the shelf life of vaccine such as polyols (WO 96/03978): sugars, including mono-, di-, tri-, or oligosaccharides and their corresponding sugar alcohols (trehalose, glucose, sucrose, lactose, fructose, galactose, mannose, maltulose, iso-maltulose, and lactulose, maltose, or dextrose and sugar alcohols of the aforementioned such as mannitol, lactitol, and maltitol). Preferred combinations of stabilizing agents (US20050080028A1) are (a) Phosphate buffered ethanol solution in combination with methionine or EDTA, (b) Tris buffered EDTA in combination with methionine or ethanol (or combinations of methionine and ethanol). Particularly preferred formulations which may be combined with the DNA and the polyols: sucrose or trehalose in demetalated water or Phosphate or Tris based buffers.

The microneedles of the vaccination/immunization matrix may include non-viral vectors including lipid-tailed peptides known as lipopeptides, peptides fused to carrier proteins such as KLH either as fusion proteins or by chemical linkage, antigens modified with a targeting tag, for example C3d or C4b binding protein, whole antigens with adjuvant, and other similar systems. Also as non-vectors can be used inorganic nanoparticles and surfaces that bind or encapsulate DNA, cationic biomolecules, including lipids, polysaccharides, polymers, and dendrimers can also electrostatically complex anionic DNA to facilitate transfection.

The microneedles of the vaccination/immunization matrix may also include additional agents, such as DNAase and RNase inhibitors to protect DNA/RNA vaccines from nucleases. An example of such inhibitor is aurinticarboxylic acid.

The vaccination/immunization matrix according to one preferred embodiment is designed for vaccination against COVID-19 disease.

The above components can be included in various combinations in the same microneedle and/or can be provided in different microneedles/matrices, and/or in a liquid/polymer injected/applied to the skin after the dissolution of microneedles.

The concentration of active components in the vaccination/immunization matrix according to one preferred embodiment, can be 0.5-1.8 µg/cm$^2$. The matrix size can vary from 1 cm$^2$ to 50 cm$^2$. To modify the dose of the active components is achieved by changing the size of the matrix, rather than changing amount of ingredients within the microneedles.

The two-step injection procedure of this invention has several advantages compared with existing ones. A major problem related to the existing microneedle matrices known in the art is long migration times of Langerhans cells to the target cells, typically more than 2 hours. Therefore, an ordinary application procedure takes about 3 hours or/and the active components have to be made to remain stable for long times which is very problematic, and deviations/errors of dose formation become great. Moreover, taking into account the spring effect of the skin that causes to pushing the microneedles of the matrix away from the skin, efficiency and accuracy of a 2-hour application procedure are very low.

The two-step application procedure disclosed here allows significantly enhanced dynamics of the molecular migration process in the skin and, in addition, reduction of deviations errors. According to a preferred embodiment of this invention the dissolvable microneedles of the vaccination/immunization matrix include polymers that become modified due to fermentation during dissolution of the microneedles. This process decreases the release time and/or increases the dissolution speed. Accordingly, an advantage of this invention is that the life-time of the active components in the vaccination/immunization matrices can be clearly shorter than in prior known solutions.

Structure of the Microneedles of the System

The microneedles at least of the skin preparation composition part (first inner matrix) and the vaccine composition part (second inner matrix) are bio-soluble by their nature. The microneedles of the fixation part component are preferably also bio-soluble. The biodegradation of microneedles made of bio-soluble polymers means that the matrix of microneedles changes its state, as a result of which the active agent in the needle enters the skin. Release of the active agent may include one or more physical and/or chemical processes, such as hydration, diffusion, phase transition, crystallization, dissolution, enzymatic reaction and/or chemical reaction.

Biodegradation can be caused by one or more of the following factors: water, body fluids, humidity, body temperature, enzymes, catalysts and/or reagents. The microneedle matrix can decompose as a result of dissolution and/or swelling and/or phase change (crystalline or amorphous), thereby breaking down or simply (increasing the penetration of the medium). The microneedle matrix may be in an amorphous or crystalline state or be partially amorphous and partially crystalline.

Figure 11:
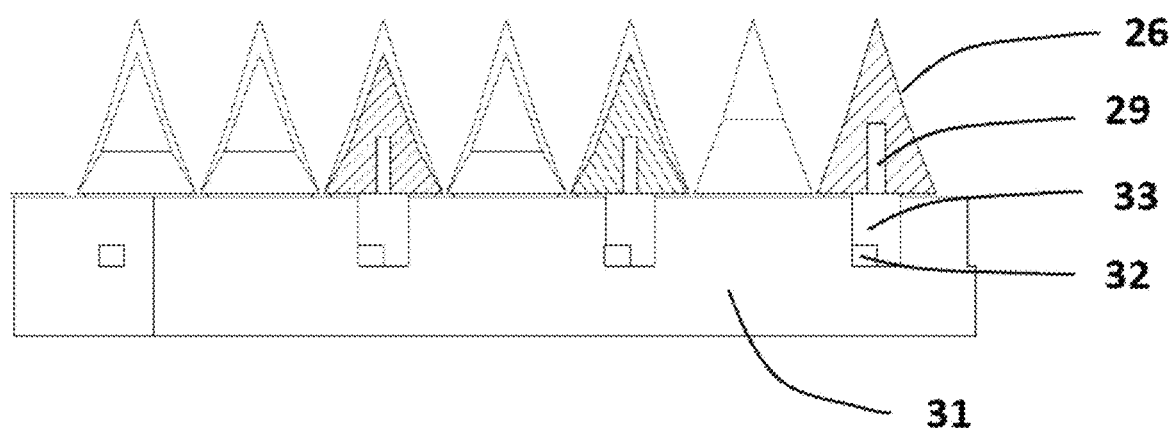
FIG. 11 shows an embodiment of the system where the microneedles 26 of an inner matrix are partially hollow i.e., equipped with vertical needle channels 29 that go parallel to the longitudinal axes of the microneedles. The base 31 of the matrix is equipped with a system of horizontal channels 32 that run parallel to the plane of the base and a second system of connecting channels 33 connecting the first system of horizontal channels 32 with the vertical needle channels 29 inside the microneedles. In this embodiment the system of horizontal channels 32 and the connecting channels 33 enables enhancing dissolution liquid (ed/-component) to enter microneedles when added or pumped into the cuvette (central volume).
Figure 12:
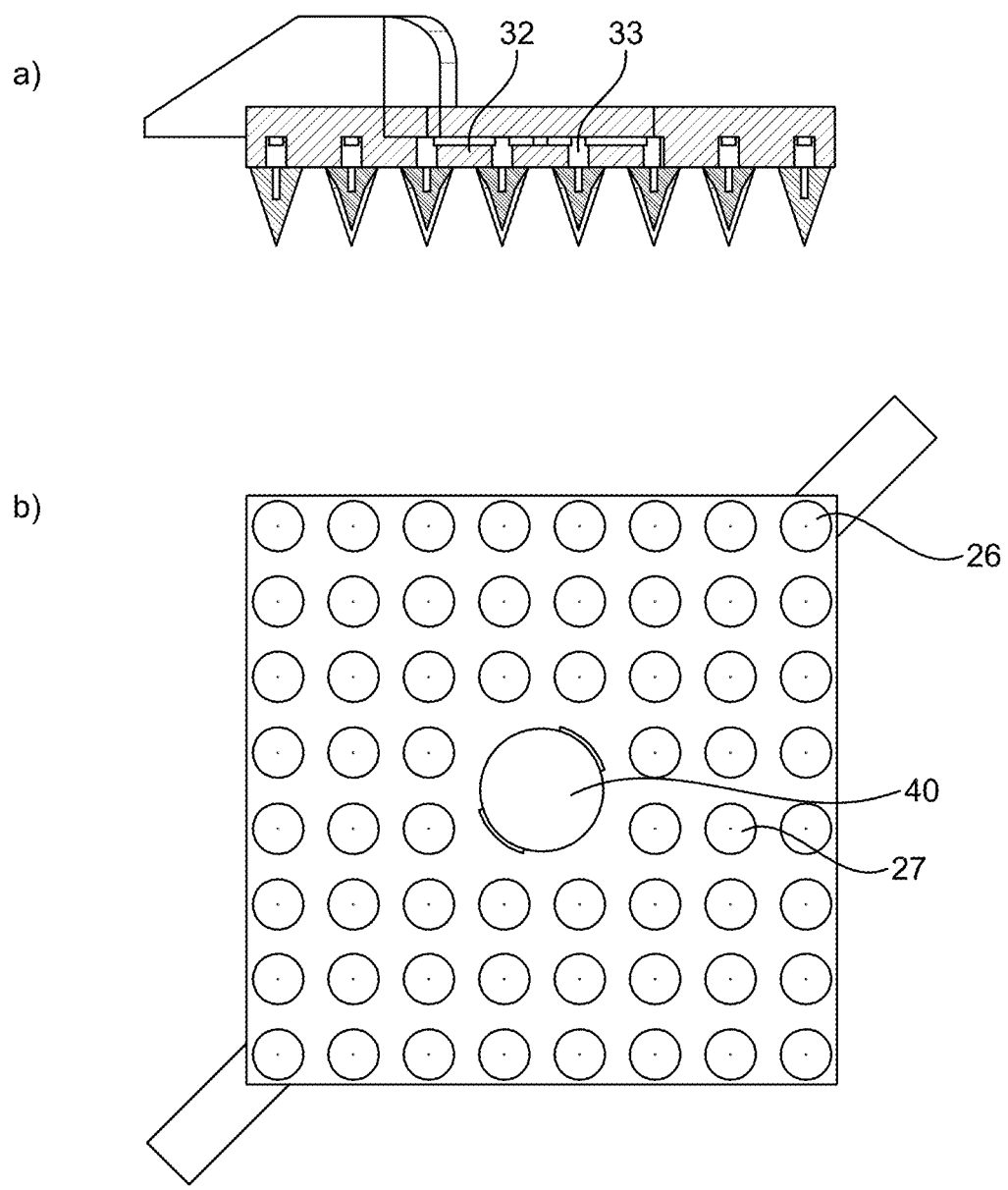
FIG. 12A-B show the inner matrix 2 equipped with the half hollow microneedles and horizontal channels 32 and connecting channels 33 for transferring a liquid active component (edl) from the cuvette (central volume) 40*a*. a) is a cross-section of the matrix and 12*b* is a bottom view of the matrix.
Figure 13:
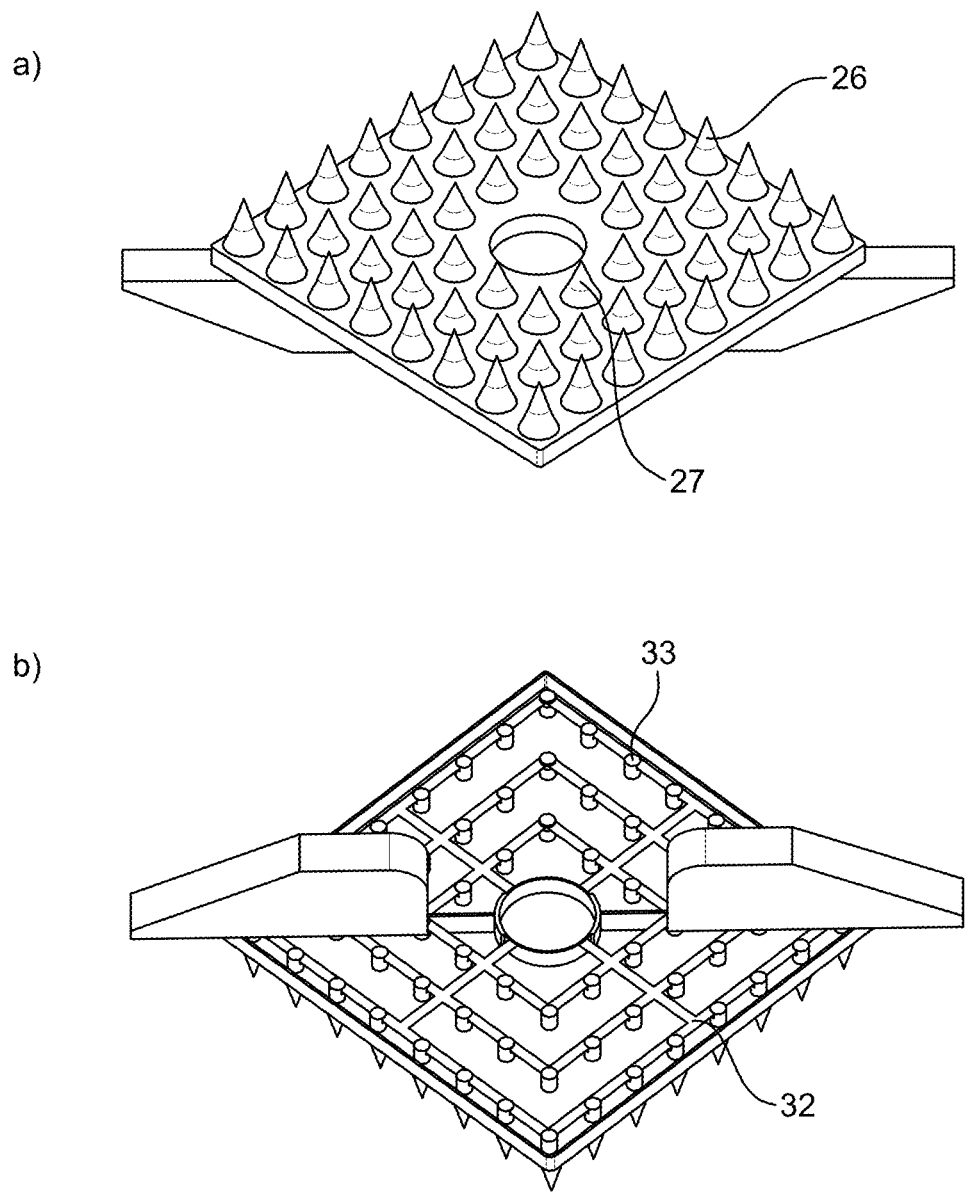
FIG. 13A-B show the inner matrix of FIG. 12A-B from two different angles: a) from the bottom revealing the microneedles 26, 27 and b) from the top revealing an example of the channels 32, 33 within the base. The base can be made of two layers; one of which can be processed separately for producing the channels and second layer set on top of the first layer to cover the open side of the vertical channels. b) shows the cuvette (central volume) 40*a* in the middle of the matrix being connected via the horizontal channels 32 to the connecting channels 33 and thereby to the microneedle vertical channels.
Figure 14:
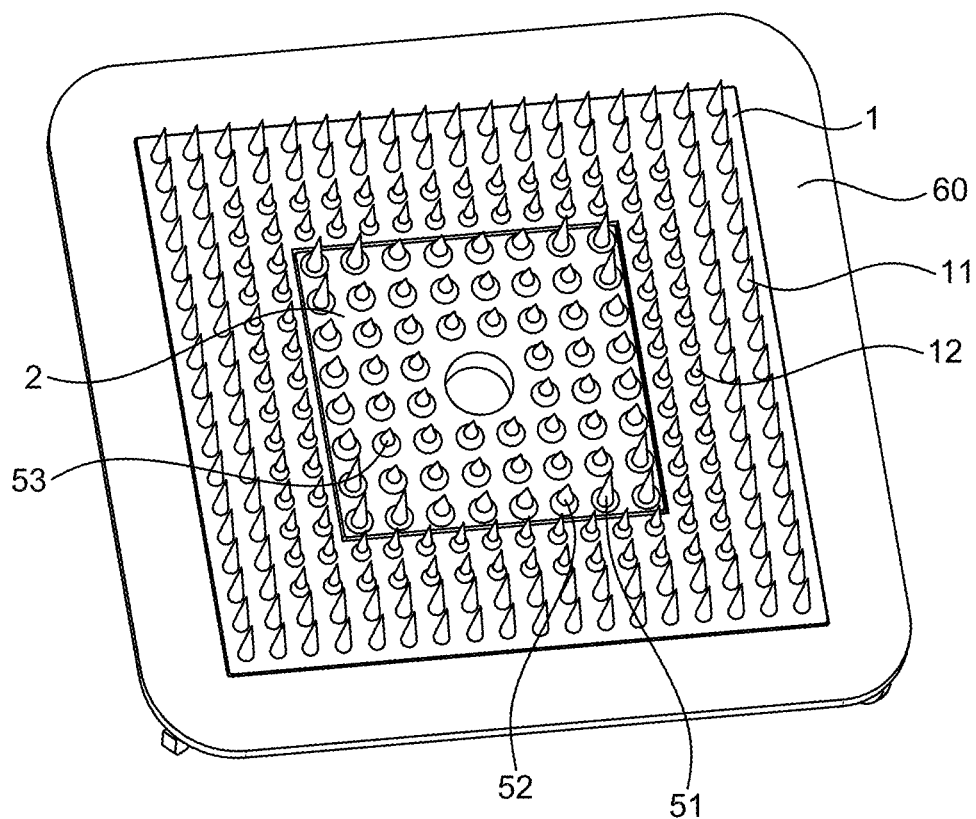
FIG. 14 shows an exemplary arrangement of different microneedle sets. Each microneedle set has its specific function and is manufactured on specific segments of the matrices. The outer matrix 1 includes microneedles 11,12. The inner matrix 2 includes microneedles 51, 52, 53. The arrangement of the microneedle sets in the matrix can vary in numbers of the microneedles, configuration, and placement positions in the matrix. In this embodiment the outer matrix 1 is installed in a frame 60 and the inner matrix 2 is inserted in the opening window area 15 of the outer matrix 1.

According to one preferred embodiment of this invention the multicomponent microneedle injection system comprises a microchannel network (illustrated e.g. in FIGS. 11-13) and comprises the channels 32, 33 within the base of one or more of the inner matrices 1. According to one embodiment the microchannel network comprises the horizontal and connecting channels one in the vaccination/immunization matrices (second inner matrix). According to another embodiment the microchannel network is only in the skin preparation matrices (first inner matrix). According to yet another embodiment all types of inner matrices include the microchannel network. In any one of these embodiments the microneedles of the respective matrix may also include the hollow vertical channels 29 connecting the needles via the connecting channels into the microchannel system. With this channel network it is possible to contribute and precisely control biodegradation of the microneedles by supplying component through a cuvette (a central volume) 40a that initiates the biodegradation.

The components provided through the microchannel systems are called here edl-component (enhancing dissolution liquid). When the edl-component is supplied to the base of a needle or to the bases of a group of needles via the microchannel systems the edl-component ensures complete or partial dissolution of the polymer of the base of the microneedle by changing the viscosity of its polymeric components. The edl-component may be composed of water, an aqueous solution of polymers-salts-sugars, and/or mixture of enzymes enhancing dissolution process and/or swelling/diffusion/enzymatic decomposition e.g. decomposition of hyaluronic acid by the hyaluronidase enzyme. As the edl-component affects the microneedle, the microneedle starts to dissolve, separation of the microneedle tip from the back and/or complete dissolution of the microneedle takes place. Along with this diffusion of an active component on or in the microneedle into the skin takes place.

According to the embodiments with the microchannel network, the bottom side of the matrix (side that is toward the skin) is equipped with microchannels (32, 33), which have connection to bases of one or more microneedles. Microchannels may be filled with an edl-component from a single reservoir (e.g. cuvette 40a) or there may be a multitude of independent systems leading to different groups of microneedles. For example, a matrix may include two different types of microneedles and one type of microneedles are connected to one microchannel network that is filled with one edl-component from one reservoir and the other type of needles are connected to another microchannel network filled with another edl-component from another reservoir. This kind of system allows for example starting biodegradation of one set of needles earlier than biodegradation of another type of microneedles by supplying different edl-components or different concentration of same edl-component to the two microchannel networks or by supplying same edl-component at different times into the microchannel networks. This system allows a wide range of variation for the use of the system.

When bio-soluble microneedles are introduced into the skin using the system of this invention, the dissolution of the microneedles will occur in almost entire volume. The tip dissolution will be triggered by interstitial skin fluid, and the microneedle base will dissolve under the action of an additional edl-component in the required volume. The volume of fluid supplied to each microneedle through the microchannels can vary from 0.1 to 50 microliter, more preferably from 1 to 20 microliters. The reservoirs from which the edl-components are supplied may be syringes or any other type of micro-dosing systems.

The embodiment including the microchannel networks provides an advantage in introducing microneedles into the aged skin, subject to age-related changes and characterized by a high degree of dehydration. Since the dissolution of microneedles in dehydrated skin occurs extremely slowly, a prolonged exposure of the system to the skin is usually necessary, which makes the vaccination process less controlled due to the possibility due to incomplete dissolution of microneedles. With an additional supply of edl-component to the base of microneedles, the application/residence time of the system on the skin is markedly reduced and provides a better controlled dissolution/disconnection of the tips of microneedles carrying the active component from the matrix.

Figure 18:
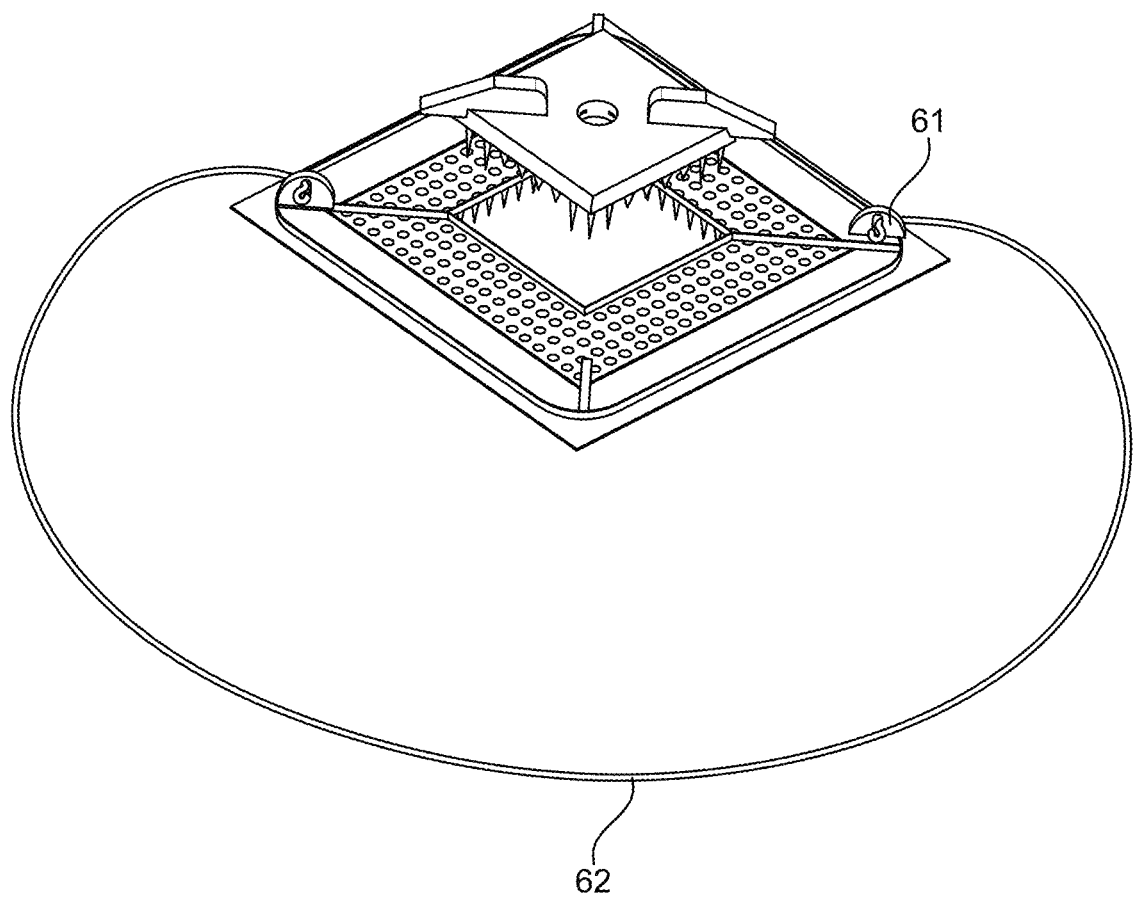
FIG. 18 shows the dissoluble microneedle drug delivery system of FIG. 16 is equipped with a fixation strip 62 for attaching the system onto forearm or shoulder.

According to another embodiment the system may contain various kinds of fixing ribbons to fix the device on a shoulder or a forearm zone for example. According to one preferred embodiment the inner matrices are equipped with rivets or fixing clamps (fixing means shown in FIGS. 16-18) at the corners of their upper side (side that is not toward the skin), from which the ribbons, tires, laces or collars are looped and tightened around the arm.

Figure 19:
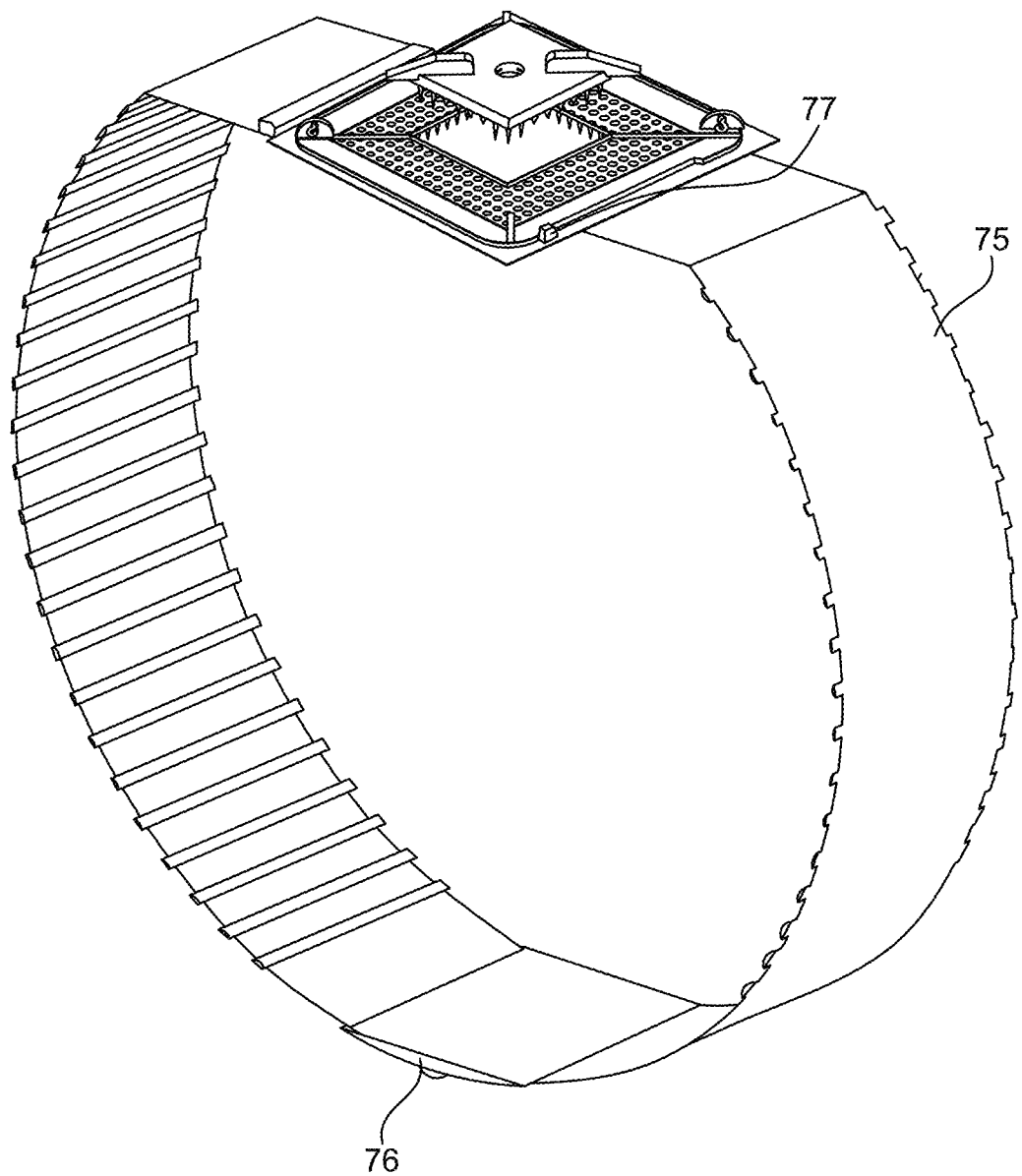
FIG. 19 shows the dissoluble microneedle drug delivery system equipped with a bracelet 75 for fixation on a human body. The bracelet has a locking mechanism 76 and is fixed to the system using, for example, mini hinges 77.

According to certain embodiments the system may also be attached to a bracelet as is shown in FIG. 19. These types of solutions are aimed to ease the use of the vaccination/immunization system of this invention by persons that are not trained for providing vaccinations/immunizations.

EXAMPLES

The following working Examples as well as the figures are included to demonstrate preferred embodiments of the invention. It should be appreciated by those of skill in the art that the techniques disclosed in the Examples and Figures represent techniques discovered by the inventors to function well in the practice of the invention, and thus can be considered to constitute preferred modes for its practice. However, those of skill in the art should, in light of the present disclosure, appreciate that many changes can be made in the specific embodiments, which are disclosed and still obtain a like or similar result without departing from the spirit and scope of the invention.

Figure 21:
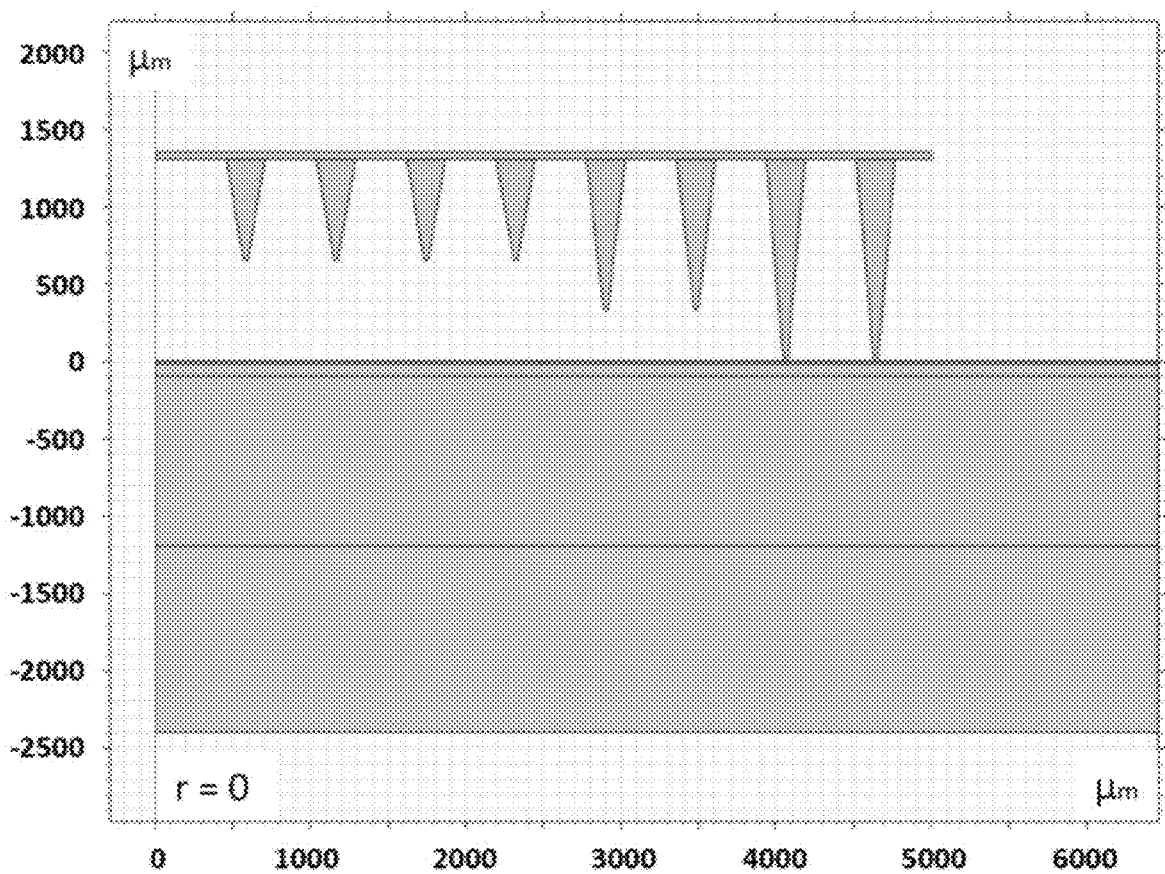
FIG. 21 shows gradient microneedle matrix. Finite element model (FEM) geometry setting of the example.
Figure 22:
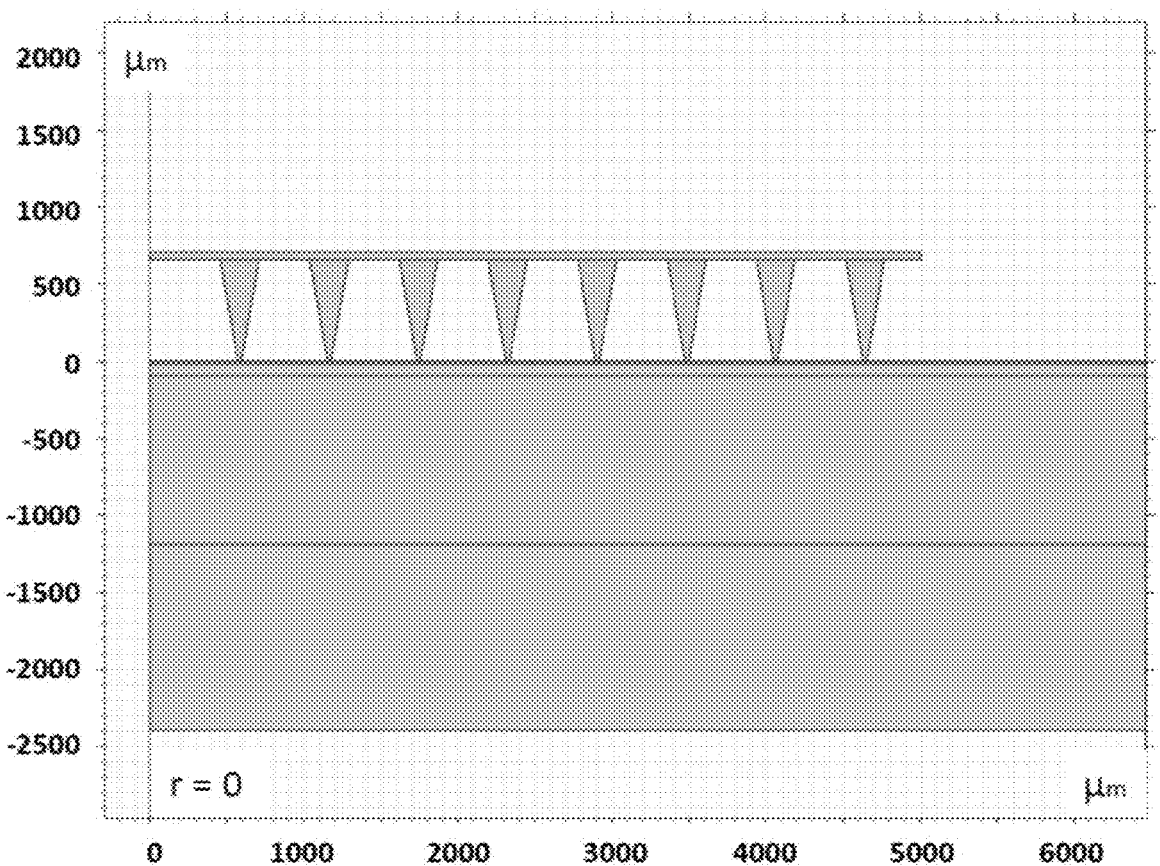
FIG. 22 shows uniform microneedle matrix. Finite element model (FEM) geometry setting of the example.
Figure 23:
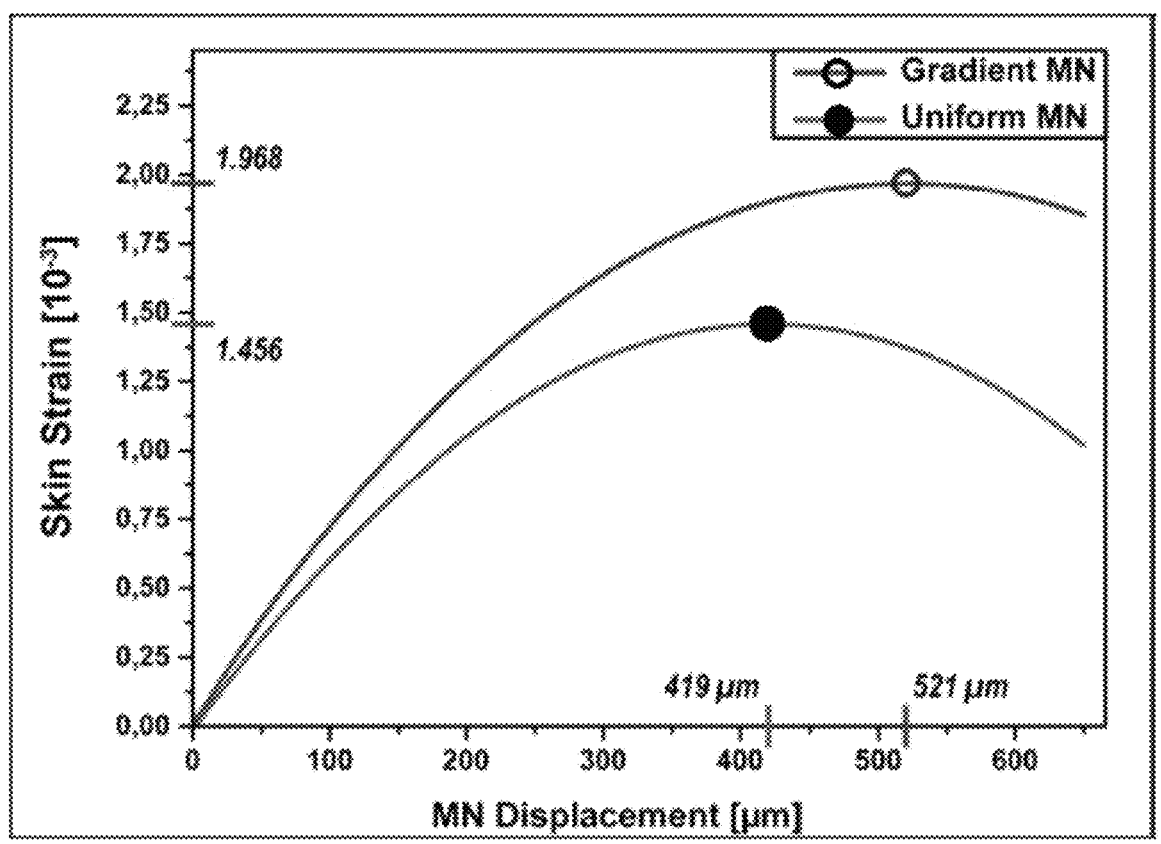
FIG. 23 shows skin strain behavior vs microneedle array displacement founded for gradient microneedle array and uniform microneedle array.

Example 1 Gradient Microneedle Profile Increases Skin Strain, Protects the Drug Carrying Microneedles from Cracking and Improves Accuracy of Dosing In order to evaluate the impact of microneedle arrays having non-uniform microneedle length on skin mechanical tension, 2D axisymmetric finite element models (FEM) of microneedle arrays and human skin layers cross-section were constructed. The results are shown in FIGS. 21-23.

Within the scope of FEM models, skin layers were modeled as 2-parameter Mooney-Rivlin hyper-elastic incompressible solids. The material of microneedle arrays was considered linear elastic having a density, Young's modulus, and Poisson ratio equaling to 1073 kg/m$^3$, 1000 MPa and 0.3 respectively. The tested microneedle arrays carrying microneedles with non-uniform length (gradient Microneedle array) was set in such a way that one half of microneedles in the cross-section (closer to Z-axis) were considered drug-carrying and having a length of 650 um while the second half of the microneedles (further away from z-axis) were treated as auxiliary microneedles which promote skin pre-tension to facilitate drug-carrying microneedles successful stratum corneum penetration (FIG. 21).

To estimate skin pre-tension effect caused by auxiliary microneedles in gradient microneedle array another FEM setting (FIG. 22) comprising microneedle matrix bearing eight microneedles of uniform length (uniform microneedles) was tested in parallel with gradient microneedle model.

To imitate microneedle insertion into skin layers, prescribed displacement boundary condition was applied to microneedle array base plate (step increment: 1 μm, displacement length 650 μm). Spring foundation boundary condition was applied to skin layers bottom imitating human adipose amortization where a fixed constraint boundary condition was applied to skin layers vertical cross-section side opposite to one allocated at z-axis. Other model boundaries remained free. Boundary probe was introduced to the top of skin imitating geometry right underneath the first pack of 4 drug-carrying microneedles near the z-axis aiming to monitor skin strain (stretching) behavior along r-axis during microneedle insertion.

The result of the foregoing FEM modeling encompassing skin strain as a result of either gradient microneedle or uniform microneedle arrays displacement toward skin layer is depicted in FIG. 23.

The result clearly shows that the use of gradient microneedle resulted in a nearly 35% increase in skin strain as compared to one uncovered during uniform microneedle usage. Also, the position of gradient maximum strain value (maximum skin stretching) was almost 100 μm deeper in comparison to the analogous value obtained from uniform microneedle behavior observation.

To this end, the result shows that implementing gradient microneedle array not only allows facilitating precise and reproducible microneedle insertion to human skin but also keeping drug-carrying needles from participating in excessive mechanical loads (auxiliary microneedles take the majority of pretension mechanical labor) preventing them from cracking and buckling, thus, increasing drug dose accuracy and reproducibility even further.

LIST OF ELEMENTS

1 outer matrix
2 first inner matrix
3 second inner matrix
8 handles
8*a* grooves
8*b* outer edge of the outer matrix
10 skin
11 fixation microneedles (longer)
12 active component carrying microneedles (shorter)
15 opening window area
20 gap 21 further type of microneedles of inner matrix
23, 24 further types of microneedles of inner matrix
26, 27 microneedles
29 vertical needle channels
31 base of matrix
32 horizontal channels
33 connecting channels
40 central hole (opening)
40a cuvette (central volume)
51,52,53 microneedles
60 frame
61 fixation mechanism
62 fixation strip
75 bracelet
76 locking mechanism
77 minihinges

What is claimed is:

1. A dissoluble microneedle drug delivery system, comprising:
an outer microneedle matrix, and at least a first and a second inner microneedle matrices;
the outer microneedle matrix having an outer microneedle matrix base and being mounted on a fixation frame and further having an opening window in its center, and an outer microneedle array affixed on the outer microneedle matrix base,
the outer microneedle array comprising microneedles of different lengths such that longest microneedles are located on outer edges of the outer microneedle matrix, and shorter microneedles are located around the opening window, the longest microneedles configured to be used for fixation of the outer microneedle matrix onto the skin and additionally for delivery of an adjuvant, and the shorter microneedles being configured to be used for adjuvant preparation of the skin;
the first inner matrix having a first inner matrix base and fitting into the opening window and having a first inner microneedle array affixed onto the first inner matrix base, the first inner microneedle array comprising a multitude of dissoluble microneedles containing skin preparation components and being configured to prepare skin underneath the first inner matrix for vaccination/immunization;
the second inner matrix being the same size as the window opening and having a second inner matrix base and a second inner microneedle array affixed onto the second inner matrix base, the second inner microneedle array comprising dissoluble microneedles containing vaccination/immunization components;
wherein the first inner matrix is dissoluble and/or removable, and the second inner matrix is configured to replace the first inner matrix after the first inner matrix is dissolved or removed.

2. The dissoluble microneedle drug delivery system of claim 1, wherein the outer matrix and the first inner matrix form one element and the first inner matrix is configured to completely dissolve and upon a complete dissolution expose the opening window for the second inner matrix to be inserted into.

3. The dissoluble microneedle drug delivery system of claim 1, wherein a basic component of the microneedles of any one of the microneedle matrices is a soluble biopolymer that dissolves in the skin due to fermentation.

4. The dissoluble microneedle drug delivery system of claim 1, wherein at least part of the microneedles of the outer matrix include an adjuvant component selected from the group comprising mineral salts, oil emulsions and surfactant-based compositions, particulate adjuvants, and endogenous human immunomodulators.

5. The dissoluble microneedle drug delivery system of claim 1, wherein the skin preparation components of the microneedles of the first inner matrix comprise factors that attract Langerhans cells, the factors including leukotrienes, galectin-1, interleukin-1b, interleukin-18, tumor necrosis factor-α, and adjuvants.

6. The dissoluble microneedle drug delivery system of claim 1, wherein the vaccination/immunization components comprise non-viral vectors including lipid-tailed peptides, peptides fused to carrier proteins, antigens modified with a targeting tag, C3d or C4b binding protein, whole antigens with adjuvant, or their combinations.

7. The dissoluble microneedle drug delivery system of claim 6, wherein the non-viral vectors include inorganic nanoparticles and surfaces that bind or encapsulate DNA, cationic biomolecules, including lipids, polysaccharides, polymers, and dendrimers with electrostatically complex anionic DNA.

8. The dissoluble microneedle drug delivery system of claim 6, wherein the microneedles of the second inner matrix additionally include stabilizing components that increase a shelf life of the vaccine, the components including polyols and sugars, the sugars including mono-, di, tri-, or oligosaccharides and their corresponding sugar alcohols.

9. The dissoluble microneedle drug delivery system of claim 1, wherein the longest microneedles of the outer matrix have lengths ranging between 600 and 1500 micrometers, and the shortest microneedles of the outer matrix have lengths ranging from 650 to 800 micrometers.

10. The dissoluble microneedle drug delivery system of claim 9, wherein diameters of the longest microneedles range between 20 to 50% of the length of the longest microneedles, and diameters of the shortest microneedles range from 30 to 60% of the length of the shortest microneedles.

11. The dissoluble microneedle drug delivery system of claim 1, wherein the first and second inner matrices have microneedles of one or more lengths ranging from 40 to 70% of the longest microneedles of the outer matrix.

12. The dissoluble microneedle drug delivery system of claim 1, wherein lengths of the microneedles of the first inner matrix are between 400 and 600 micrometers, and diameters of the microneedles of the first inner matrix ranges from 50 to 75% of the lengths of the microneedles of the first inner matrix.

13. The dissoluble microneedle drug delivery system of claim 1, wherein the array of microneedles of the first inner matrix comprises microneedles of at least two different lengths, such that longer microneedles are located closer to the outer edges of the first inner matrix while the shorter needles are located in the center of the first inner matrix.

14. The dissoluble microneedle drug delivery system of claim 1, wherein a length of the microneedles defined by a vertical axis of the microneedles gradually or stepwise decrease from an outer edge of the outer matrix inwards toward center of the first or the second inner matrix inserted in the opening window, thereby forming a crater or colosseum-like profile shape, respectively.

15. The dissoluble microneedle drug delivery system of claim 1, further comprising at least one handle for installation of the first and/or second inner matrices into the opening window of the outer matrix.

16. The dissoluble microneedle drug delivery system of claim 1, further comprising a hole a center of at least the first inner microneedle matrix for providing liquid components through the hole into a gap between the first inner microneedle matrix base and surface of the skin.

17. The dissoluble microneedle drug delivery system of claim 1, wherein the first and/or the second inner microneedle matrix has a cuvette connected to a channel system within at least one inner matrix, the channel system comprising vertical channels at least in part of the microneedles of the first and/or the second inner microneedle array and the base of the at least one inner matrix has horizontal channels, and the vertical channels and the horizontal channels are connected allowing an entry for enhancing dissolution liquid (edl) components from the cuvette via the channel system into the microneedles of the microneedle array of the at least one inner matrix to enhance dissolution of the microneedles of the microneedle array of the at least one inner matrix.

18. The dissoluble microneedle drug delivery system of claim 1, further comprising fixation mechanisms with a fixation strip or a bracelet for fixation of the delivery system on a shoulder or an arm.

19. A method of transdermal vaccination of skin, said method comprising:
   a) attaching an outer matrix of the dissoluble microneedle drug delivery system of claim 1 onto the skin,
   b) preparing the skin by increasing its hydration of epidermis, and attracting Langerhans cells to a vaccination area by attaching the first inner matrix comprising an array of microneedles comprising adjuvant components,
   c) removing the first inner matrix or allowing the first inner matrix to fully dissolve, and
   d) attaching the second inner matrix comprising an array of microneedles comprising vaccination/immunization components.

20. The method of claim 19, wherein microneedle arrays of the system have a gradient profile having longest microneedles at the edges of the outer matrix and shortest in center area of at least one of the inner matrices.

21. The method of claim 19, wherein the method further comprises providing liquid components through a central hole of at least the first inner matrix into a gap between the base of the at least the first inner matrix and surface of the skin.

22. The method of any of claims 19, wherein the method further comprises providing enhancing dilution liquids (edl) via a cuvette connected to a channel network within the base of at least one inner matrix, the channel network comprising vertical needle channels in at least some microneedles and horizontal channels within the base of the at least one inner matrix, and the vertical and horizontal channels being connected, thereby allowing entry to the enhancing dilution liquid to the microneedles and enhancing dissolution of the microneedles.

23. The method of claim 19, wherein vaccination/immunization components include non-viral vectors including lipid-tailed peptides, peptides fused to carrier proteins, antigens modified with a targeting tag, C3d or C4b binding protein, whole antigens with adjuvant, or their combinations.

24. The method of claim 19, wherein the second inner matrix comprises vaccination/immunization components against COVID 19-disease.

* * * * *